(12) United States Patent
Wang et al.

(10) Patent No.: US 8,980,216 B2
(45) Date of Patent: Mar. 17, 2015

(54) COVALENTLY FUNCTIONALIZED CARBON NANOSTRUCTURES AND METHODS FOR THEIR SEPARATION

(75) Inventors: YuHuang Wang, Laurel, MD (US); Alexandra H. Brozena, Takoma Park, MD (US); Shunliu Deng, College Park, MD (US); Yin Zhang, Hyattsville, MD (US)

(73) Assignee: University of Maryland, College Park, College Park, MD (US)

(*) Notice: Subject to any disclaimer, the term of this patent is extended or adjusted under 35 U.S.C. 154(b) by 0 days.

(21) Appl. No.: 13/439,029

(22) Filed: Apr. 4, 2012

(65) Prior Publication Data

US 2013/0072669 A1    Mar. 21, 2013

Related U.S. Application Data

(60) Provisional application No. 61/471,570, filed on Apr. 4, 2011, provisional application No. 61/471,572, filed on Apr. 4, 2011, provisional application No. 61/491,818, filed on May 31, 2011.

(51) Int. Cl.
| | |
|---|---|
| *C01B 31/04* | (2006.01) |
| *C07C 51/353* | (2006.01) |
| *C07C 57/40* | (2006.01) |
| *C07H 1/00* | (2006.01) |
| *B82Y 40/00* | (2011.01) |

(52) U.S. Cl.
CPC ............. *C07C 51/353* (2013.01); *C07C 57/40* (2013.01); *C07H 1/00* (2013.01); *Y10S 977/748* (2013.01); *Y10S 977/847* (2013.01); *B82Y 40/00* (2013.01); *Y10S 977/745* (2013.01)

USPC .............. 423/447.3; 977/745; 423/447.1; 977/748; 977/847

(58) Field of Classification Search
USPC .............. 423/447.1, 447.3; 977/748, 847
See application file for complete search history.

(56) References Cited

U.S. PATENT DOCUMENTS

| | | |
|---|---|---|
| 7,125,533 B2 | 10/2006 | Khabashesku et al. |
| 7,494,639 B2 | 2/2009 | Smalley et al. |
| 7,740,826 B2 | 6/2010 | Khabashesku et al. |

(Continued)

FOREIGN PATENT DOCUMENTS

WO    WO 2010089395 A2 *  8/2010

OTHER PUBLICATIONS

Deng, S. et al. "Diameter-dependent, progressive alkylcarboxylation of single-walled carbon nanotubes". Chem. Commun., 2011, 47, 758-760. Online Nov. 11, 2010*

(Continued)

*Primary Examiner* — Richard M Rump
(74) *Attorney, Agent, or Firm* — Sterne, Kessler, Goldstein & Fox P.L.L.C.

(57) ABSTRACT

The present invention is directed to carbon nanostructures, e.g., carbon nanotubes, methods of covalently functionalizing carbon nanostructures, and methods of separating and isolating covalently functionalized carbon. In some embodiments, carbon nanotubes are reacted with alkylating agents to provide water soluble covalently functionalized carbon nanotubes. In other embodiments, carbon nanotubes are reacted with a thermally-responsive agent and exposed to light in order to separate carbon nanotubes of a specific chirality from a mixture of carbon nanotubes.

6 Claims, 21 Drawing Sheets

(56) References Cited

U.S. PATENT DOCUMENTS

| | | | |
|---|---|---|---|
| 7,758,841 | B2 | 7/2010 | Billups et al. |
| 7,976,816 | B2 | 7/2011 | Khabashesku et al. |
| 2007/0110658 | A1 | 5/2007 | Liang et al. |
| 2007/0278448 | A1* | 12/2007 | Chari et al. ............ 252/299.01 |
| 2012/0114549 | A1* | 5/2012 | Chenevier ................ 423/447.1 |

OTHER PUBLICATIONS

Liang, F. "A Convenient Route to Functionalized Carbon Nanotubes". Nano Letters 2004 vol. 4, No. 7 1257-1260.*
D. Wunderlich, F. Hauke and A. Hirsch. "Preferred functionalization of metallic and small-diameter single walled carbon nanotubes via reductive alkylation". J. Mater. Chem. , 2008, 18, 1493-1497.*
Covalent Sidewall Functionalization of Single Wall Carbon Nanotubes Rajesh K. Saini,Ivana W. Chiang,Haiging Peng,R. E. Smalley,W. E. Billups,*, Robert H. Hauge, and, and John L. Margrave Journal of the American Chemical Society 2003 125 (12), 3617-3621.*
Zeta-Potential Measurements of Surfactant-Wrapped Individual Single-Walled Carbon Nanotubes Brian White, Sarbajit Banerjee, Stephen O'Brien, Nicholas J. Turro, and, and Irving P. Herman the Journal of Physical Chemistry C2007111 (37), 13684-13690.*
Allen, M.J. et al., "Honeycomb Carbon: A Review of Graphene," *Chem. Rev. 110*:132-145, American Chemical Society (2010).
Arnold, M.S. et al., "Sorting carbon nanotubes by electronic structure using density differentiation," *Nat. Nanotechnol. 1*:60-65, Nature Publishing Group (2006).
Bachilo, S.M. et al., "Structure-Assigned Optical Spectra of Single-Walled Carbon Nanotubes," *Science 298*:2361-2366, American Association for the Advancement of Science (2002).
Baker, S.E. et al., "Covalently Bonded Adducts of Deoxyribonucleic Acid (DNA) Oligonucleotides with Single-Wall Carbon Nanotubes: Synthesis and Hybridization," *Nano Lett. 2*:1413-1417, American Chemical Society (2002).
Banerjee, S. and Wong, S.S., "Rational Sidewall Functinalization and Purification of Single-Walled Carbon Nanotubes by Solution-Phase Ozonolysis," *J. Phys. Chem. B 106*:12144-12151, American Chemical Society (2002).
Baughman, R.H. et al., "Carbon Nanotubes—the Route Toward Applications," *Science 297*:787-792, American Association for the Advancement of Science (2002).
Bethune, D.S. et al., "Cobalt-catalysed growth of carbon nanotubes with single-atomic-layer walls," *Nature 363*:605-607, Nature Publishing Group (1993).
Birch, A.J., "Reduction by Dissolving Metals. Part I," *J. Chem. Soc.*, pp. 430-436, RSC Publishing (1944).
Bronzena, A.H. et al., "Outer Wall Selectively Oxidized, Water-Soluble Double-Walled Carbon Nanotubes," *JACS 132*:3932-3938, American Chemical Society (2010).
Chattopadhyay, J. et al., "Synthesis of Water-Soluble PEGylated Single-Walled Carbon Nanotubes," *Chem. Mater. 18*:5864-5868, American Chemical Society (2006).
Chen, J. et al., "Solution Properties of Single-Walled Carbon Nanotubes," *Science 282*:95-98, American Association for the Advancement of Science (1998).
Chung, C.-H. et al., "Oxidation of Step Edges on Si(001-$c$(4 X 2))," *PRL 97*:036103-1-036103-4, The American Physical Society (2006).
Cognet, L. et al., "Stepwise Quenching of Exciton Fluorescence in Carbon Nanotubes by Single-Molecule Reactions," *Science 316*:1465-1468, American Association for the Advancement of Science (2007).
Davis, V.A. et a., "True solutions of single-walled carbon nanotubes for assembly into macrospcopic materials,"*Nat. Nanotechnol. 4*:830-834, Nature Publishing Group (2009).
Deng, S. et al., "Confined propagation of covalent chemical reactions on single-walled carbon nanotubes," *Nat. Commun. 2*:1-6, Macmillan Publishers Limited (Jul. 12, 2011).
Deng, S. et al., "Diameter-dependent, progressive alkylcarboxylation of single-walled carbon nanotubes," *Chem. Commun. 47*:758-760, The royal Society of Chemistry (Published on Nov. 11, 2010 at http://pubs.rsc.org / doi:10.1039/C0CC03896B).
Dresselhaus, M.S. et al., "Raman Spectroscopy of Carbon Nanotubes in 1997 and 2007," *J. Phys. Chem. C 111*:17887-17893, American Chemical Society (2007).
Duggal, R. and Pasquali, M., "Dynamics of Individual Single-Walled Carbon Nanotubes in Water by Real-Time Visualization," *PRL 96*:246104-1-246104-4, The American Physical Society (2006).
Farmer, D.B. and Gordon, R.G., "ALD of High-κ Dielectrics on Suspended Functionalized SWNTs," *Electrochemical and Solid-State Letters 8*:G89-G91, The Electrochemical Society (2005).
García-Lastra, J.M. et al., "Conductance of Sidewall-Functionalized Carbon Nanotubes: Universal Dependence on Adsorption Sites," *PRL 101*:236806-1-236806-4, The American Physical Society (2008).
Goldsmith,B.R. et al., "Conductance-Controlled Point Functionalization of Single-Walled Carbon Nanotubes," *Science 315*:77-82, American Association for the Advancement of Science (2007).
Green, A.A. and Hersam, M.C., "Ultracentrifugation of single-walled nanotubes," *Mater. Today 10*:59-60, Elsevier Ltd. (2007).
Hersam, M.C., "Progress towards monodisperse single-walled carbon nanotubes," *Nat. Nanotechnol. 3*:387-394, Macmillan Publishers Limited (2008).
Hirlekar, R. et al., "Carbon Nanotubes and Its Applications: A Review," *Asian J. Pharm. Clin. Res. 2*:17-27, Abhilasha Jain (2009).
Hughes, M.E. et al., "Optical Absorption of DNA-Carbon Nanotube Structures," *Nano Lett. 7*:1191-1194, American Chemical Society (2007).
Huxtable, S.T. et al., "Interfacial heat flow in carbon nanotube suspensions," *Nat. Mater 2*:731-734, Nature Publishing Group (2003).
Iimima, S., "Helical microtubes of graphitic carbon," *Nature 354*:56-58, Nature Publishing Group (1991).
Iijima, S. and Ichihashi, T., "Single-shell carbon nanotubes of 1-nm diameter," *Nature 363*:603-605, Nature Publishing Group (1993).
Kamaras, K. et al., "Covalent Bond Formation to a Carbon Nanotube Metal," *Science 301*:1501, American Association for the Advancement of Science (2003).
Kanungo, M. et al., "Suppression of Metallic Conductivity of Single-Walled Carbon Nanotubes by Cycloaddition Reactions," *Science 323*:234-237, American Association for the Advancement of Science (2009).
Karousis, N. and Tagmatarchis, N., "Current Progress on the Chemical Modification of Carbon Nanotubes," *Chem. Rev. 110*:5366-5397, American Chemical Society (2010).
Kelly, K.F. et al., "Insight into the mechanism of sidewall functionalization of single-walled nanotubes: an STM study," *Chem. Phys. Lett. 313*:445-450, Elsevier Science B.V. (1999).
Khare, R. and Bose, S., "Carbon Nanotube Based Composites—A Review," *Journal of Minerals & Materials Characterization & Engineering 4*:31-46, Scientific Research Publishing (2005).
Leskelä, M. and Ritala, M., "Atomic Layer Deposition Chemistry: Recent Developments and Future Challenges," *Angew. Chem. Int. Ed. 42*:5548-5554, Wiley-VCH Verlag GmbH & Co. KGaA, Weinheim (2003).
Liang, F. et al., "A Convenient Router to Functionalized Carbon Nanotube," *Nano Lett. 4*:1257-1260, American Chemical Society (2004).
López-Benzanilla, A. et al., "Effect of the Chemical Functionalization on Charge Transport in Carbon Nanotubes at the Mesoscopic Scale," *Nano Lett. 9*:940-944, American Chemical Society (2009).
McEuen, P.L., "Single-wall carbon nanotubes," *Physics World*, pp. 31-36, IOP Publishing Ltd. (2000).
Merkoçi, A., "Carbon Nanotubes in Analytical Sciences," *Microcim. Acta 152*:157-174, Springer-Verlag (2005).
Moniruzzaman, M. et al., "Tuning the Mechanical Properties of SWNT/Nylon 6,10 Composites with Flexible Spacers at the Interface," *Nano Lett. 7*:1178-1185, American Chemical Society (2007).
Murakoshi, K. and Okazaki, K., "Electrochemical potential control of isolated single-walled carbon nanotubes on gold electrode," *Electrochim. Acta 50*:3069-3075, Elsevier Ltd. (2005).

(56) References Cited

OTHER PUBLICATIONS

Nikolaev, P. et al., "Gas-phase catalytic growth of single-walled carbon nanotubes from carbon monoxide," *Chem. Phys. Lett. 313*:91-97, Elsevier Science B.V. (1999).

O'Connell, M.J. et al., "Chiral selectivity in the charge-transfer bleaching of single-walled carbon-nanotube spectra," *Nat. Mater. 4*:412-418, Nature Publishing Group (2005).

Oron-Carl, M. et al., "On the Electron-Phonon Coupling of Individual Single-Walled Carbon Nanotubes," *Nano Lett. 5*:1761-1767, American Chemical Society (2005).

Peng, X. et al., "Optically active single-walled carbon nanotubes," *Nat. Nanotechnol. 2*:361-365, Nature Publishing Group (2007).

Rubloff, G.W. et al., "Defect Microchemistry at the $SiO_2$/Si Interface," *PRL 58*:2379-2382, The American Physical Society (1987).

Sánchez-Pomales, G. et al., "DNA-Wrapped Carbon Nanotubes: From Synthesis to Applications," in *Nanotechnology and Nanomaterials*, "Carbon Nanotubes", Ch. 35, Marulanda, J.M., ed., InTech Europe, Rijeka, Croatia (2010).

Sharma, R. et al., "Anomalously Large Reactivity of Single Graphene Layers and Edges toward Electron Transfer Chemistries,"*Nano Lett. 10*:398-405, American Chemical Society (2010).

Strano, M.S. et al., "Electronic Structure Control of Single-Walled Carbon Nanotube Functionalization," *Science 301*:1519-1522, American Association for the Advancement of Science (2003).

Terrones, M., "Science and Technology of the Twenty-First Century: Synthesis, Properties, and Applications of Carbon Nanotubes,"*Annu. Rev. Mater. Res. 33*:419-501, Annual Reviews (2003).

Tu, X. et al., "DNA sequence motifs for structure-specific recognition and separation of carbon nanotubes," *Nat. Lett. 460*:250-253, Macmillan Publishers Limited (2009).

Usrey, M.L. et al., "Evidence for a Two Step Mechanism in Electronically Selective Single-Walled Carbon Nanotube Reactions," *J. Am. Chem. Soc. 127*:16129-16135, American Chemical Society (2005).

Wang, Y. et al., "Nanofabrication beyond Electronics," *ACS Nano 3*:1049-1056, American Chemical Society (2009).

Wang, Y. et al., "A Highly Selective, one-Pot Purification Method for Single-Walled Carbon Nanotubes," *J. Phys. Chem. B 111*:1249-1252, American Chemical Society (2007).

Wang, X. et al., "Atomic Layer Deposition of Metal Oxides on Pristine and Functionalized Graphene,"*J. Am. Chem. Soc. 130*:8152-8153, American Chemical Society (2008).

Williams, K.A. et al., "Carbon nanotubes with DNA recognition," *Nature 420*:761, Nature Publishing Group (2002).

Wunderlich. D. et al., "Preferred functionalization of metallic and small-diameter single walled carbon nanotubes via reductive alkylation," *J. Mater. Chem. 18*:1493-1497, The Royal Society of Chemistry (2008).

Xu, Y. et al., "Double-Stranded DNA Single-Walled Carbon Nanotube Hybrids for Optical Hydrogen Peroxide and Glucose Sensing," *J. Phys. Chem. C 111*:8638-8643, American Chemical Society (2007).

Zhang, Y. et al., "Laser-Heating Effect on Raman Spectra of Individual Suspended Single-Walled Carbon Nanotubes," *J. Phys. Chem. C 111*:1988-1992, American Chemical Society (2007).

Zhang, Y. and Wang, Y., "Gold-Substrate-Enhanced Scanning Electron Microscopy of Functionalized Single-Wall Carbon Nanotubes," *J. Phys. Chem. Lett. 2*:885-888, American Chemical Society (Mar. 30, 2011).

Zhao, B., "Synthesis and Characterization of Water Soluble Single-Walled Carbon Nanotube Graft Copolymers," *J. Am. Chem. Soc. 127*:8197-8203, American Chemical Society (2005).

Zheng, M. and Semke, E.D., "Enrichment of Single Chirality Carbon Nanotubes," *J. Am. Chem. Soc. 129*:6084-6085, American Chemical Society (2007).

Ziegler, K.J. et al., "Controlled Oxidative Cutting of Single-Walled Carbon Nanotubes," *J. Am. Chem. Soc. 127*:1541-1547, American Chemical Society (2005).

Zimmerman, H.E. and Wang, P.A., "The Regioselectivity of the Birch Reduction," *J Am. Chem. Soc. 115*:2205-2216, American Chemical Society (1993).

George, S.M. et al., "Surface Chemistry for Atomic Layer Growth," *J Phys. Chem. 100*:13121-13131, American Chemical Society (1996).

Schild, H.G., "Poly(*N*-Isopropylacrylamide): Experiment, Theory and Application," *Prog. Polyrn. Sci. 17*:163-249, Pergamon Press Ltd. (1992).

Troullier, N. and Martins, J.L., "Efficient pseudopotentials for plane-wave calculations," *Phys. Rev. B. 43*:1993-2006, The American Physical Society (1991).

Yang, Z. et al., "Birch Reduction of Graphite. Edge and Interior Functionalization by Hydrogen," *J. Am. Chem. Soc. 134*:18689-18694 American Chemical Society (2012).

Ziegler, K.J. et al., "Controlled Oxidative Cutting of Single-Walled Carbon Nanotubes," *J. Am. Chem. Soc. 127*:1541-1547 American Chemical Society (2005).

\* cited by examiner

RX = Br(CH$_2$)$_5$COOH
Br(CH$_2$)$_5$CH$_3$
C$_2$H$_5$OH

COVALENTLY FUNCTIONALIZED CARBON NANOSTRUCTURES AND METHODS FOR THEIR SEPARATION

STATEMENT REGARDING FEDERALLY SPONSORED RESEARCH OR DEVELOPMENT

This invention was made with government support under DESC001160 awarded by the Department of Energy. The government has certain rights to this invention.

REFERENCE TO SEQUENCE LISTING SUBMITTED ELECTRONICALLY

The content of the electronically submitted sequence listing (Name: 17970700003_Sequence_Listing_11262012_ASCII.txt; Size: 707 bytes; and Date of Creation: Nov. 26, 2012) filed with the application is incorporated herein by reference in its entirety.

BACKGROUND OF THE INVENTION

1. Field of the Invention

The present disclosure relates generally to carbon nanostructures, methods of covalently functionalizing carbon nanostructures, and methods of separating and isolating covalently functionalized carbon nanostructures.

2. Background

Carbon nanotubes (CNTs) are self-assembling nanostructures comprised of graphite sheets rolled up into cylinders (Iijima, Nature 354:56-58 (1991)). Such nanostructures are termed single-walled CNTs (SWNTs) if they are comprised of a single cylindrical tube (Iijima et al., Nature 363:603-605 (1993); Bethune et al., Nature 363:605-607 (1993)). CNTs comprising two or more concentric tubes are termed double-walled CNTs (DWNTs) and multi-walled CNTs (MWNTs), respectively. Regarding SWNTs, the diameter of these species can typically range from 0.4 nm to ca. 3 nm, and the length from ca. 10 nm to centimeters.

CNTs possess outstanding structural, mechanical, and electronic properties due to the unique combination of their dimension, structure, and topology. Thus, CNTs have found use in a wide variety of applications including conductive and high-strength composites, electrode materials for high capacity batteries, efficient field emission displays and radiation sources, and functional nanoscale devices (Baughman et al., Science 297:787-792 (2002)).

Separating CNTs by structure is a challenge. Within a small diameter range (0.4-2 nm), a SWNT can have over 300 possible chiral structures, each uniquely indexed by a pair of integers (n,m). Two SWNTs, e.g., (10,10) vs. (11,9), may differ in diameter by less than 0.01 nm, amounting to a mere 0.15% difference in density. Distinguishing this minute structural difference is currently beyond the reach of even the most successful separation methods developed (Hersam, Nature Nanotechnology 3:387-394 (2008)) which rely on surface properties (Peng et al., Nature Nanotechnology 2:361-365 (2007): Zheng and Semke, J. Am. Chem. Soc. 129:6084-6085 (2007)) or density discrimination (Arnold et al., Nature Nanotechnology 1:60-65 (2006)).

There exists a need to develop methods to synthesize a single type of CNT displaying only semiconductor or metallic properties. While some progress is being made in this field, there is still no perfect method. In response to synthetic limitations, several chemical separations methods have been developed to purify CNT samples of different chiralities or electronic character from bulk samples of mixed species. DNA wrapped CNTs can be chirally resolved and separated by modifying the DNA nucleotide sequence and passing the sample through an ion exchange column (Tu et al., Nature 460:250-253 (2009)). This approach produces perhaps the purest samples of semiconductors. However, the procedure is optimized for semiconductor CNTs and fails to achieve a similar level of separation for metallic CNTs. Additionally, the usage of DNA is expensive and yields are limited to between 0.1 to 0.8 µg of chirally resolved semiconducting CNTS for every 100 µg of raw CNT sample. Ultracentrifugation of surfactant encapsulated CNTs has also been shown capable of sorting CNTs by buoyant density, which allows for the enrichment of metallic types (Arnold et al., Nature Nanotechnology 1:60-65 (2006); Green and Hersam, Mater. Today 10:59-60 (2007)). The technique has shown reasonable yields to the µg level and scalability is predicted to increase with the use of industrial size centrifuges which could increase processing scale to gram levels. However, the use of surfactants and ultracentrifugation ultimately limit scalability and requires excessive sonication which can damage CNTs and diminish their attractive properties.

In addition to these physical separation methods, a number of metallic selective chemistries have been developed, including diazonium (Strano et al., Science 301:1519-1522 (2003); Usrey et al., J. Am. Chem. Soc. 127:16129-16135 (2005)) and divalent chemistries such as [2+2] cycloadditions (Kanungo et al., Science 323:234-237 (2009)) and carbene cycloadditions (Kamaras et al., Science 301:1501 (2003)) which have been shown to effectively react with metallic CNTs prior to semiconductors. It is hypothesized that this metallic selectivity occurs as a result of the increased electron demand for these reagents. For instance, diazonium salts appear to undergo a charge-transfer complex before covalent addition with CNTs and the positively charged transition state is stabilized by the higher energy-level electrons at the Fermi level of metallic CNTs (Usrey et al., J. Am. Chem. Soc. 127:16129-16135 (2005)). However, these highly selective chemistries fail to provide a means to physically separate the functionalized metallic CNTs from semiconductor counterparts. The selectivity is typically lost long before enough functional groups can be coupled to the nanotubes to effect separation.

BRIEF SUMMARY OF THE INVENTION

In one aspect, the disclosure provides methods of covalently functionalizing carbon nanostructures, e.g., CNTs, by introducing one or more defects on the carbon nanostructure and then reacting the carbon nanostructure with an alkylating agent, e.g., 6-bromohexanoic acid. Applicants have found that the alkylation reaction propagates from the vicinity of the one or more defects/existing functional groups in the carbon nanostructure, rather than by the addition of new functional groups at random sites on the carbon nanostructure. This propagation chemistry can be used to create carbon nanostructures having alternating sections (or segments) of functionalized and intact (unfunctionalized) areas of the nanotube.

In another aspect, the present disclosure provides a CNT covalently functionalized with —$(CH_2)_m CO_2 R^2$, and a method of preparing a compound functionalized with —$(CH_2)_m CO_2 R^2$, wherein:

m is an integer from 4-30; and $R^2$ is hydrogen or a monovalent cation.

In another aspect, the disclosure provides methods of separating and isolating one type or chirality of CNT from mixtures of CNTs. For example, the incorporation hydrophilic moieties on selected CNTs allow those particular functionalized CNTs to be physically separated from a mixture of intrinsically hydrophobic CNTs, e.g., by water extraction. The unique electronic and optical properties of CNTs can also be used to separate and isolate a CNT having a particular chirality from a mixture of CNTs. In one embodiment, the method of preparing one type or chirality of CNT free from other CNTs comprises reacting a mixture of CNTs with a compound having Formula I:

$$X\text{---}(CH_2)_m\text{---}R^1 \qquad \text{I}$$

wherein:
X is halo;
m is an integer from 1-30;
$R^1$ is $CO_2R^2$; and
$R^2$ is hydrogen or a monovalent cation;
partitioning the product of reaction of the mixture of CNTs with Formula I in water and an organic solvent; and separating the water layer from the organic solvent layer, wherein the water layer comprises a CNT covalently functionalized with —$(CH_2)_n CO_2R^2$ having a particular type or chirality.

In another embodiment, the method of preparing one type or chirality of CNT essentially free from other CNTs comprises reacting or mixing a mixture of CNTs with a thermally-responsive reagent; exposing the CNT products of the reaction or mixing to a particular wavelength of light or a particular range of wavelengths of light; and separating the CNTs that absorb light from the CNTs that do not absorb light, wherein the CNTs that absorb light cause a physical change in the thermally-responsive reagent by localized heating of the CNT.

DETAILED DESCRIPTION OF THE INVENTION

Figure 1:
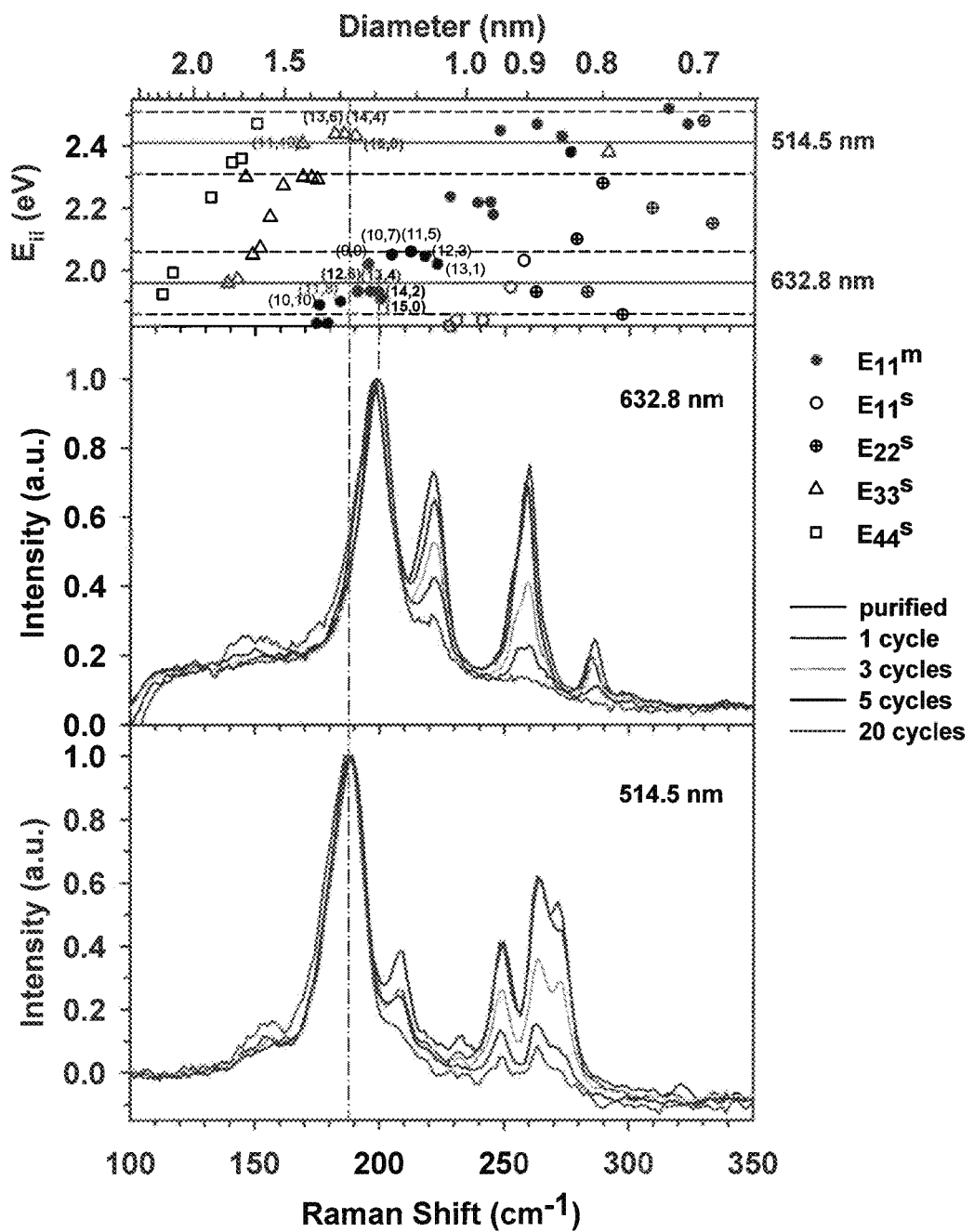
FIG. 1 is a Kataura plot (top panel) and two Raman spectra normalized to the RBM peak with the highest intensity for 632.8 nm (middle panel) and 524.5 nm (bottom panel) excitation lines showing the evolution of diameter-dependent alkylcarboxylation of CNTs.

In one embodiment, the disclosure provides a method of producing a covalently functionalized carbon nanostructure, the method comprising:
a) introducing one or more defects onto a carbon nanostructure; and
b) reacting the carbon nanostructure comprising the one or more defects with an alkylating agent,
wherein covalent functionalization propagates from the vicinity of the one or more defects.

In another embodiment, the carbon nanostructure is selected from the group consisting of CNT, graphitic nanostructure, and graphene.

In another embodiment, the carbon nanostructure is a CNT. In another embodiment, the CNT is selected from the group consisting of SWNTs, DWNTs, few-walled CNTs, and MWNTs. In one embodiment, the CNT is single-walled. In another embodiment, the CNT is metallic. In another embodiment, the CNT is semiconducting.

In another embodiment, the covalent functionalization propagates from the one or more defects and/or existing functional groups to create alternating sections or segments of functionalized and intact regions of the covalently functionalized carbon nanostructure, e.g., a covalently functionalized CNT.

In another embodiment, the one or more defects are introduced onto a pristine carbon nanostructure. In another embodiment, the pristine carbon nanostructure is a pristine CNT.

In another embodiment, the one or more defects introduced onto the carbon nanostructure are sp$^3$ defects.

In another embodiment, the one or more defects are introduced by treating the carbon nanostructure with H$_2$O$_2$ and HCl.

In another embodiment, the one or more defects are introduced by treating the carbon nanostructure with a diazonium salt, e.g., 4-bromobenzenediazonium tetrafluoroborate, 4-nitrobenzenediazonium tetrafluoroborate, 4-carboxylbenzenediazonium tetrafluoroborate, 4-tert-butylbenzenediazonium tetrafluoroborate, 4-methylbenzenediazonium tetrafluoroborate, benzenediazonium tetrafluoroborate, 4-methoxybenzenediazonium tetrafluoroborate.

In another embodiment, the one or more defects are introduced by treating the carbon nanostructure with a source of radicals, e.g., peroxide decomposition initiating alkyl halide radical addition.

In another embodiment, the one or more defects are introduced by treating the carbon nanostructure with a source of fluorine, e.g., F$_2$ or XeF$_3$.

In another embodiment, the one or more defects are introduced by treating the carbon nanostructure with a source of atomic oxygen, atomic hydrogen, electrons, or ions.

In another embodiment, reacting the carbon nanostructure comprising the one or more defects with an alkylating agent comprises combining the carbon nanostructure comprising said one or more defects, the alkylating agent, liquid ammonia, and an alkali metal, e.g., sodium.

In another embodiment, the alkylating agent is an organic halide, e.g., an alkyl halide.

In another embodiment, the organic halide is a compound having Formula I:

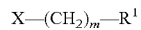

wherein:
X is halo;
m is an integer from 1-30;
R$^1$ is H or CO$_2$R$^2$; and
R$^2$ is hydrogen or a monovalent cation, e.g., Na$^+$, Li$^+$, Na$^+$.

In another embodiment, the one or more defects are introduced selectively into one CNT type or chirality that is part of a mixture of CNTs. For example, in mixture of CNTs, one or more defects are selectively introduced onto a SWNT and not a DWNT, one or more defects are selectively introduced onto a metallic SWNT and not a semiconducting SWNT, one or more defects is selectively introduced onto a small-diameter SWNT and not a large-diameter SWNT, etc.

In another embodiment, the one or more defects are selectively introduced onto a SWNT, a DWNT, a metallic SWNT, a semiconducting SWNT, or a small-diameter SWNT.

In another embodiment, the disclosure provides a CNT covalently functionalized with —$(CH_2)_mCO_2R^2$,
wherein:
m is an integer from 4-30; and
$R^2$ is hydrogen or a monovalent cation.

In another embodiment, m is an integer from 4-20. In another embodiment, m is an integer from 4-10. In another embodiment, m is an integer from 4-8.

In another embodiment, m is 5.

In another embodiment, $R^2$ is hydrogen, $Na^+$, or $Li^+$.

In other embodiment, m is 5 and $R^2$ is $Na^+$.

In another embodiment, the CNT covalently functionalized with —$(CH_2)_mCO_2R^2$ is soluble in water. The water solubility the CNT covalently functionalized with —$(CH_2)_m CO_2R^2$ is about 10 mg/L to about 5,000 mg/L, e.g., about 100 mg/L to about 4,500 mg/L, e.g., about 500 mg/L to about 3,500 mg/L, e.g., about 1,000 mg/L to about 3,500 mg/mL, e.g., about 2,500 mg/L to about 3,500 mg/L as determined by centrifugation in conjunction with UV-Vis-NIT spectroscopy. In another embodiment, the water solubility of the CNT covalently functionalized with —$(CH_2)_nCO_2R^2$ is about 500 mg/L, about 1,000 mg/L, about 1,500 mg/L, about 2,000 mg/L, about 2,500 mg/L, about 3,000 mg/L, about 3,100 mg/L, about 3,200 mg/L, about 3,300 mg/L, about 3,400 mg/L, or about 3,500 mg/L. Water soluble CNTs have important applications in biology and medicine, e.g., for use as drug delivery and biosensing platforms.

In another embodiment, the CNT covalently functionalized with —$(CH_2)_nCO_2R^2$ is a SWNT, a DWNT, a metallic SWNT, a semiconducting SWNT, or a small-diameter SWNT.

In another embodiment; the CNT covalently functionalized with —$(CH_2)_mCO_2R^2$ is substantially pure. In another embodiment, the CNT covalently functionalized with —$(CH_2)_mCO_2R^2$ is pure.

In another embodiment, the disclosure provides a method of preparing a CNT covalently functionalized with —$(CH_2)_m CO_2R^2$, the method comprising reacting a CNT with a compound having Formula I:

X—$(CH_2)_m$—$R^1$  I wherein:
X is a halo;
m is an integer from 4-30;
$R^1$ is $CO_2R^2$ and
$R^2$ is hydrogen or a monovalent cation.

In another embodiment, the method of preparing a CNT covalently functionalized with —$(CH_2)_mCO_2R^2$ further comprises partitioning the CNT covalently functionalized with —$(CH_2)_mCO_2R^2$ in water and an organic solvent.

In another embodiment, the method of preparing a CNT covalently functionalized with —$(CH_2)_mCO_2R^2$ further comprises separating the water layer from the organic solvent layer.

In another embodiment, the method of preparing a CNT covalently functionalized with —$(CH_2)_mCO_2R^2$ further comprises isolating the CNT covalently functionalized with —$(CH_2)_mCO_2R^2$.

In another embodiment, the disclosure provides a method of separating a particular CNT type or chirality from a mixture of CNTs, the method comprising:

a) reacting a mixture of CNTs with a compound having Formula I:

X—$(CH_2)_m$—$R^1$  I wherein:
X is halo;
m is an integer from 1-30;
$R^1$ is $CO_2R^2$; and
$R^2$ is hydrogen or a monovalent cation;
b) partitioning the product of a) in water and an organic solvent; and
c) separating the water layer from the organic solvent layer, wherein said water layer comprises a CNT covalently functionalized with —$(CH_2)_nCO_2R^2$ having a particular type or chirality.

In another embodiment, one or more defects are selectively introduced onto a particular CNT type or chirality, e.g., a SWNT, a DWNT, a metallic SWNT, a semiconducting SWNT, a small-diameter SWNT, before reacting the mixture of CNTs with the compound having Formula I.

In another embodiment, the method further comprises isolating the CNT covalently functionalized with —$(CH_2)_m CO_2R^2$ having a particular type or chirality from the water layer.

Figure 21:
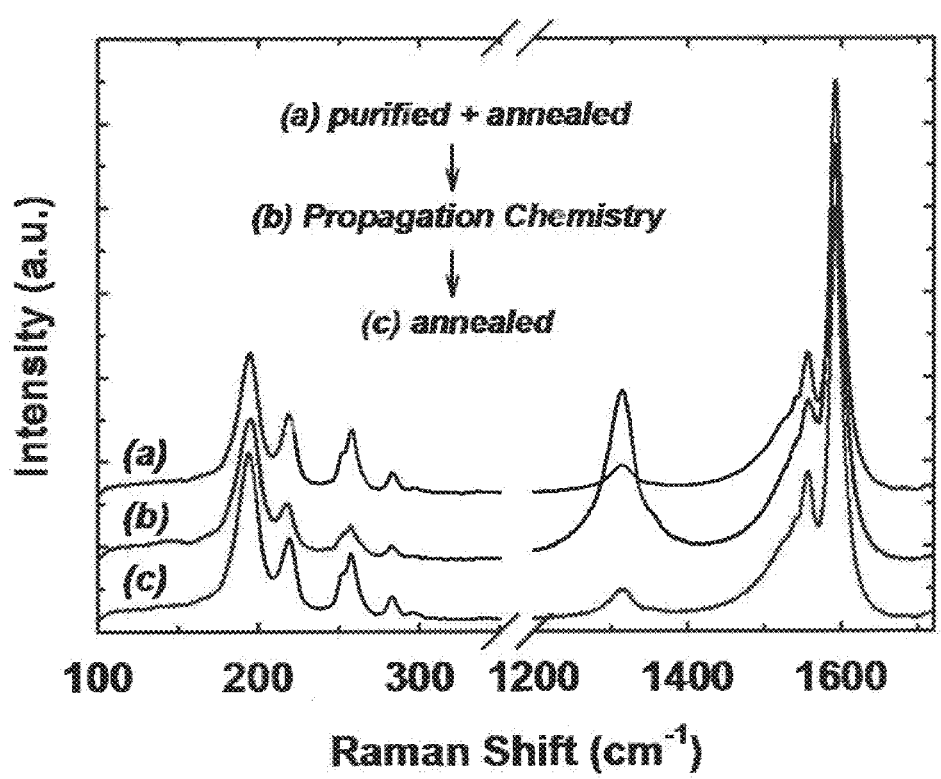
FIG. 21 is Raman spectra showing the reversibly of —(CH$_2$)$_m$CO$_2$R$^2$ functionalization of CNTs.

In another embodiment, the method further comprises removing the —$(CH_2)_mCO_2R^2$ group from the covalently functionalized CNT to provide a pristine CNT having a particular type or chirality. In one embodiment, the —$(CH_2)_m CO_2R^2$ group is removed by heating (annealing), e.g., at temperature of from about 100° C. to about 1,000° C., about 300° C. to about 800° C., or about 500° C. to about 700° C. In another embodiment, the —$(CH_2)_mCO_2R^2$ group is removed by heating at a temperature of about 100° C., about 200° C., about 300° C., about 400° C., about 500° C., about 600° C., about 700° C., about 800° C., about 900° C., or about 1,000° C. In one embodiment, the —$(CH_2)_mCO_2R^2$ group is removed under an inert atmosphere such as nitrogen or argon. The Raman scattering spectra of —$(CH_2)_mCO_2R^2$-functionalized CNTs before and after annealing shows recovery of the pristine structure as indicated by a decrease in the D-band and simultaneous increase in the G-peak (FIG. 21).

In another embodiment, the reacting the mixture of CNTs with a compound having Formula I is repeated one or more times before the product of this reaction is partitioned with water and an organic solvent, e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 25 times, 30 times, 35 times, 40 times, 45 times, 50 times, or more times. Without wishing to be bound by theory, repeating (recycling) this reaction one or more times progressively adds more —$(CH_2)_m$—$CO_2R^2$ groups to a particular CNT type or chirality via propagation from one or more defects initially introduced onto that CNT type or chirality in a selective fashion.

In another embodiment, the organic solvent is an aliphatic organic solvent. In another embodiment, the organic solvent is selected from the group consisting of pentane, hexane, heptane, cyclohexane, and toluene, or mixtures thereof. In another embodiment, the organic solvent is hexane.

In another embodiment, the mixture of CNTs is reacted with a compound having Formula I in the presence of liquid ammonia and an alkali metal. In one embodiment, the alkali metal is sodium.

In another embodiment, the compound having Formula I is 6-bromohexanoic acid.

In another embodiment, the CNT covalently functionalized with —$(CH_2)_mCO_2R^2$ having a particular type or chirality is selected from the group consisting of SWNT, DWNT, multi-walled CNT, metallic SWNT, semiconducting SWNT, small-diameter SWNT, and large-diameter SWNT.

In another embodiment, the CNT covalently functionalized with —$(CH_2)_mCO_2R^2$ is isolated in substantially pure form. In another embodiment, the CNT covalently functionalized with —$(CH_2)_mCO_2R^2$ is isolated in pure form.

In another embodiment, the disclosure provides a method of separating a particular CNT type or chirality from a mixture of CNTs, the method comprising:

a) reacting or mixing a mixture of CNTs with a thermally-responsive reagent;

b) exposing the product of the reacting or mixing to a particular wavelength of light or a particular range of wavelengths of light; and c) separating those CNTs that absorb light from the those CNTs that do no not absorb light, wherein said CNTs that absorb light cause a physical change in said thermally-responsive reagent, i.e., the thermally-responsive reagent functions as a chemical tag.

In another embodiment, the range of wavelengths is from about 300 to about 500 nm, from about 500 to about 800 nm, or from about 800 to about 1,400 nm.

In another embodiment, the CNTs that absorb light are separated from said CNTs that do not absorb light using affinity chromatography.

In another embodiment, affinity chromatography comprises magnetic beads or other separation platform well known in the art. In another embodiment, the affinity chromatography comprises immobilized single-stranded DNA (ssDNA).

In another embodiment, the thermally-responsive reagent selected from the group consisting of oligomeric compound, pyrene derivative, and polymer. In another embodiment, the thermally-responsive reagent is double stranded DNA (dsDNA).

In another embodiment, the CNTs that absorb light are semiconducting SWNTs.

In certain aspects, the disclosure is directed to the following Particular Embodiments:

I. A method comprising:
a) introducing one or more defects onto a carbon nanostructure; and
b) reacting said carbon nanostructure comprising said one or more defects with an alkylating agent,
wherein covalent functionalization propagates from said one or more defects to produce a covalently functionalized carbon nanostructure.

II. The method of Particular Embodiment I, wherein said carbon nanostructure is selected from the group consisting of CNT, graphitic nanostructure, and graphene.

III. The method of Particular Embodiment II, wherein said carbon nanostructure is a CNT.

IV. The method of Particular Embodiment III, wherein said CNT is selected from the group consisting of SWNT, DWNT, few-walled CNT, and MWNT.

V. The method of Particular Embodiment I, wherein covalent functionalization propagates from said one or more defects to create alternating sections of functionalized and intact regions of said covalently functionalized carbon nanostructure.

VI. The method of Particular Embodiment I, where said one or more defects are introduced onto a pristine carbon nanostructure.

VII. The method of Particular Embodiment I, wherein said one or more defects are $sp^3$ defects.

VIII. The method of Particular Embodiment I, wherein said one or more defects are introduced by treating said carbon nanostructure with $H_2O_2$ and HCl.

IX. The method of Particular Embodiment 1, wherein said one or more defects are introduced by treating said carbon nanostructure with a diazonium salt.

X. The method of Particular Embodiment XI, wherein said diazonium salt is selected from the group consisting of 4-bromobenzenediazonium tetrafluoroborate, 4-nitrobenzenediazonium tetrafluoroborate, 4-carboxylbenzenediazonium tetrafluoroborate, 4-tert-butylbenzenediazonium tetrafluoroborate, 4-methylbenzenediazonium tetrafluoroborate, benzenediazonium tetrafluoroborate, 4-methoxybenzenediazonium tetrafluoroborate.

XI. The method of Particular Embodiment I, wherein said one or more defects are introduced by treating said carbon nanostructure with a source of radicals, e.g., wherein source of radicals is peroxides.

XII. The method of Particular Embodiment I, wherein said one or more defects are introduced by treating said carbon nanostructure with a source of fluorine.

XIII. The method of Particular Embodiment XII, wherein source of fluorine are selected from the group consisting of $F_2$ and $XeF_3$.

XIV. The method of Particular Embodiment I, wherein said one or more defects are introduced by treating said carbon nanostructure with a source of atomic oxygen, atomic hydrogen, electrons, or ions.

XV. The method of Particular Embodiment I, wherein said reacting comprises combining said carbon nanostructure comprising said one or more defects, said alkylating agent, liquid ammonia, and an alkali metal.

XVI. The method of Particular Embodiment XVI, wherein said alkali metal is sodium.

XVII. The method of Particular Embodiment XV, wherein said alkylating agent is an organic halide.

XVIII. The method of Particular Embodiment XVII, wherein said organic halide is a compound having Formula I:

$$X-(CH_2)_m-R^1 \qquad \text{I}$$

wherein:
X is halo;
m is an integer from 1-30;
$R^1$ is H or $CO_2R^2$; and
$R^2$ is hydrogen or a monovalent cation.

XIX. The method of Particular Embodiment III, wherein said one or more defects are introduced onto one CNT type or chirality that is part of a mixture of CNTs.

XX. The method of Particular Embodiment XIX, wherein said one or more defects are introduced onto a single-walled CNT.

XXI. The method of Particular Embodiment XIX, wherein said one or more defects is introduced onto a double-walled CNT.

XXII. The method of Particular Embodiment XIX, wherein said one or more defects is introduced onto a metallic single-walled CNT.

XXIII. The method of Particular Embodiment XIX, wherein said one or more defects is introduced onto a semiconducting single-walled CNT XXIV. The method of Particular Embodiment XIX, wherein said one or more defects is introduced onto a small-diameter single-walled CNT.

XXV. A CNT covalently functionalized with —$(CH_2)_m$ $CO_2R^2$,
wherein:
m is an integer from 4-30; and
$R^2$ is hydrogen or a monovalent cation.
XXVI. The CNT of Particular Embodiment XXV that is single-walled.
XXVII. The CNT of Particular Embodiment XXVI that is metallic.
XXVIII. The CNT of Particular Embodiment XXVI that is semiconducting.
XXIX. The CNT of Particular Embodiment XXVI that is small diameter.
XXX. The CNT of Particular Embodiment XXV, wherein n is 5 and $R^2$ is selected from the group consisting of hydrogen, $Li^+$, and $Na^+$.
XXXI. The CNT of Particular Embodiment XXV isolated in essentially pure form.
XXXII. The CNT of Particular Embodiment XXXI isolated in substantially pure form.
XXIII. The CNT of Particular Embodiment XXXII isolated in pure form.
XXXIV. A method comprising:
a) reacting a CNT with a compound having Formula I:

$$X\text{—}(CH_2)_m\text{—}R^1 \qquad I$$

wherein:
X is a halo;
m is an integer from 4-30;
$R^1$ is $CO_2R^2$; and
$R^2$ is hydrogen or a monovalent cation;
b) partitioning the product of a) in water and an organic solvent;
c) separating the water layer from the organic solvent layer; and
d) isolating said CNT of Particular Embodiment XXV.
XXXV. The method of Particular Embodiment XXXIV, wherein a) is repeated one or more times before b).
XXXVI. The method of Particular Embodiment XXXIV, wherein one or more defects is introduced onto said CNT before a).
XXXVII. A method comprising:
a) reacting a mixture of CNTs with a compound having Formula I:

$$X\text{—}(CH_2)_m\text{—}R^1 \qquad I$$

wherein:
X is halo;
m is an integer from 1-30;
$R^1$ is $CO_2R^2$; and
$R^2$ is hydrogen or a monovalent cation;
b) partitioning the product of a) in water and an organic solvent; and
c) separating the water layer from the organic solvent layer,
wherein said water layer comprises a CNT covalently functionalized with —$(CH_2)_nCO_2R^2$ having a particular type or chirality.
XXXVIII. The method of Particular Embodiment XXXVII, wherein a) is repeated one or more times before b).
XXXIX. The method of Particular Embodiment XXXVII, wherein one or more defects are introduced onto one CNT type or chirality that is part of said mixture of CNTs before a).
XL. The method of Particular Embodiment XXXVII further comprising isolating said CNT covalently functionalized with —$(CH_2)_mCO_2R^2$ from the water layer of c).

XLI. The method of Particular Embodiment XL further comprising heating said CNT covalently functionalized with —$(CH_2)_mCO_2R^2$ to provide a pristine CNT having a particular type or chirality.
XLII. The method of Particular Embodiment XXXVII, wherein said CNT covalently functionalized with —$(CH_2)_m$ $CO_2R^2$ is single-walled.
XLIII. The method of Particular Embodiment XXXVII, wherein said CNT covalently functionalized with —$(CH_2)_m$ $CO_2R^2$ is metallic.
XLIV. The method of Particular Embodiment XXXVII, wherein said CNT covalently functionalized with —$(CH_2)_m$ $CO_2R^2$ is semiconducting.
XLV. The method of Particular Embodiment XXXVII, wherein said CNT covalently functionalized with —$(CH_2)_n$ $CO_2R$ is small diameter.
XLVI. The method of Particular Embodiment XXXVII, wherein said organic solvent is selected from the group consisting of pentane, hexane, heptane, cyclohexane, and toluene.
XLVII. The method of Particular Embodiment XXXVII, wherein said compound having Formula I is 6-bromohexanoic acid.
XLVIII. The method of Particular Embodiment XXXVII, wherein said CNT covalently functionalized with —$(CH_2)_m$ $CO_2R^2$ is essentially pure.
XLIX. The method of Particular Embodiment XLVIII, wherein said particular CNT is substantially pure.
L. The method of Particular Embodiment XLIX, wherein said particular CNT is pure.
LI. A method comprising:
a) reacting or mixing a mixture of CNTs with a thermally-responsive reagent;
b) exposing the product of a) to a particular wavelength of light or a particular range of wavelengths of light; and
c) separating the CNTs that absorb light from the CNTs that do not absorb light,
wherein said CNTs that absorb light cause a physical change in said thermally-responsive reagent.
LII. The method of Particular Embodiment LI, wherein said CNTs that absorb light are separated from said CNTs that do not absorb light using affinity chromatography.
LIII. The method of Particular Embodiment LII, wherein said affinity chromatography comprises functionalized magnetic beads.
LIV. The method of Particular Embodiment LI, wherein said thermally-responsive reagent selected from the group consisting of oligomeric compound, pyrene derivative, and polymer.
LV. The method of Particular Embodiment LW, wherein said thermally-responsive reagent is double stranded DNA.
LVI. The method of Particular Embodiment LI, wherein said CNT is a semiconducting SWNT.
LVII. The method of Particular Embodiment LVI, wherein said semiconducting SWNT has a specific chirality.

DEFINITIONS

The term "carbon nanostructure" as used herein refers to allotropic forms of carbon, with or without impurities, which take the form of single-walled or multi-walled tubes, cylinders, spheres, crystals, sheets, rods, or other structures. In one embodiment, the carbon nanostructure is a fullerene, a CNT, a graphene, or a nanostructure containing $sp^2$-bonded carbon. In another embodiment, the carbon nanostructure of the present disclosure is a CNT.

The term "carbon nanotube" or "CNT" as used herein refers to an allotropic form of carbon with a cylindrical nanostructure (see, for example, Baughman et al., *Science* 297: 787-192 (2002)).

CNTs are differentiated by their chiral vector (n, m). For the purpose of the present disclosure, CNTs can be categorized into different types, e.g., according to their diameter, wall number, and/or electrical properties. CNTs can also be differentiated according to their chirality.

In one embodiment, the CNT is a single-walled CNT (SWNT). In another embodiment, the CNT is a double-walled CNT (DWNT). In another embodiment, the CNT is a few-walled CNT. In another embodiment, the CNT is a multi-walled CNT.

In one embodiment, the CNT is metallic or semiconducting. In another embodiment, the CNT is a metallic SWNT. In another embodiment, the CNT is a semiconducting SWNT.

In one embodiment, the CNT is a SWNT that is classified as small diameter or large diameter. In one embodiment a small diameter SWNT has a diameter of less than 1 nm, e.g., less than about 0.9 nm, less than about 0.8 nm, less than about 0.7 nm, less than about 0.6 nm, or less than about 0.5 nm. In one embodiment, a large diameter single-walled CNT has a diameter of more than 1 nm, e.g., more than about 1.1 nm, more than about 1.2 nm, more than about 1.3 nm, more than about 1.4 nm, more than about 1.5 nm, more than about 1.6 nm, more than about 1.7 nm, more than about 1.8, nm, more than about 1.9 nm, or more than about 2.0 nm.

The term "chirality" as used herein refers to a SWNT having discrete (n,m) values.

The term "pristine carbon nanotube" as used herein refers to a CNT that has no observable surface modifications except at the nanotube ends, e.g., as determined by Raman spectroscopy or other methods known in the art.

The term "composition" or "mixture" as used herein in refers to a population of CNTs comprising more than one type, e.g., single-walled, double-walled, metallic, semiconducting, small-diameter, larger-diameter, and/or chirality.

The term "partitioning" as used herein refers to a liquid-liquid extraction method to separate compounds based on their relative solubilities in two different immiscible liquids, e.g., water and hexane.

The term "essentially pure" as used herein refers to a CNT or covalently functionalized CNT comprising more than about 75% of one type, e.g., metallic SWNT, e.g., small diameter SWNT, and/or chirality and less than about 25% of other types, e.g., semiconducting SWNT, e.g., large diameter SNWT and/or chiralities as established using conventional analytical methods, e.g., Raman spectroscopy, routinely used by those of skill in the art. In one embodiment, the amount of other types and/or chiralities in an essentially pure CNT or covalently functionalized CNT is less than about 24%, less than about 23%, less than about 22%, less than about 21%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, or less than about 0.5%.

The term "substantially pure" as used herein refers to a CNT or covalently functionalized CNT comprising more than about 95% of one type, and/or chirality and less than about 5% of other types and/or chiralities as established using conventional analytical methods, e.g., Raman spectroscopy, routinely used by those of skill in the art. In one embodiment, the amount of other types and/or chiralities in a substantially pure CNT or covalently functionalized CNT is less than about 5%, less than about 4%, less than about 3%, less than about 2%, less than about 1%, or less than about 0.5%.

The term "pure" as used herein refers to a CNT or covalently functionalized CNT comprising one type and/or chirality and no detectable amount of other types and/or chiralities as established using conventional analytical methods, e.g., Raman spectroscopy, routinely used by those of skill in the art. In certain embodiments, the amount of other types, and/or chiralities in a pure CNT or covalently functionalized CNT is less than about 1%, less than about 0.9%, less than about 0.8%, less than about 0.7%, less than about 0.6%, less than about 0.5%, less than about 0.4%, less than about 0.3%, less than about 0.2%, or less than about 0.1%.

The term "thermally-responsive reagent" as used herein refers to oligomeric compounds, e.g., an oligomer or polymer of ribonucleic acid (RNA) or deoxyribonucleic acid (DNA), pyrene derivatives, or polymers, e.g., poly(N-isopropylacrylamide), that undergo a physical change when exposed to different temperatures, e.g., are heated above about 10° C., about 15° C., about 20° C., about 25° C., about 30° C., about 35° C., about 40° C., about 45° C., about 50° C., about 55° C., about 60° C., about 70° C., or about 80° C. Oligomeric compounds suitable for use in the present disclosure are described U.S. Pat. No. 8,133,876. In one embodiment, the thermally-responsive reagent is double-stranded DNA.

The term "defect" as used herein refers to an irregularity in the $sp^2$ bonding network of a carbon nanostructure. See P. G. Collins, in Oxford Handbook of Nanoscience and Technology: Frontiers and Advances. Narlikar, A. V. & Fu, Y. Y. Eds. (Oxford Press, 2010). In one embodiment, the defect is a $sp^3$ defect.

The term "halo" as used herein refers to F, Cl, Br, or I. In one embodiment, the halo is Cl, Br, or I. In another embodiment, the halo is Cl. In another embodiment, the halo is Br. In another embodiment, the halo is I.

The term "alkylating agent" as used herein refers to reagent capable of placing an alkyl group onto a nucleophilic site, including, but not limited to, organic halides, dialkyl sulfates such as dimethyl sulfate, diethyl sulfate; and di-n-propyl sulfate; and alkyl or aryl sulfonates such as methyl-p-toluenesulfonate, ethyl methanesulfonate, or n-propyl methanesulfonate. In one embodiment, the alkylating agent is an organic halide, e.g., an alkyl halide, such as methyl bromide, ethyl bromide, n-propyl bromide, methyl iodide, ethyl iodide, n-propyl bromide, methyl iodine, benzyl bromide, bromoacetic acid, 3-bromopropionic acid, 4-bromobutanoic acid, 5-bromopentanoic acid, 6-bromohexanoic acid, 7-bromoheptanoic acid, and the like. In one embodiment, the alkylating agent is 6-bromohexanoic acid.

The term "alkali metal" as used herein refers to Li, Na, and K. In one embodiment, the alkali metal is Li. In another embodiment, the alkali metal is Na. In another embodiment, the alkali metal is K.

The term "covalently functionalized CNT" as used herein refers to CNT having surface functional groups attached to the nanotube carbon sidewall through a covalent bond. A covalently functionalized CNT may also be referred to as a derivative CNT.

The term "about," as used herein, includes the recited number±10%. Thus, "about 10" means 9 to 11.

EXAMPLES

Example 1

Confined Propagation of Covalent Chemical Reactions on SWNTs

This example describes a diameter-dependent, alkylcarboxylation reaction of SWNTs by adapting the Billups-Birch reductive alkylation (Liang et al., *Nano Lett.* 4:1257-1260 (2004)) into a recycling procedure. This alkylcarboxylation chemistry allowed the functionalization of HiPco SWNTs progressively from the smaller diameter nanotubes towards the larger ones. The addition of alkylcarboxylic acid functional groups to the carbon lattice made SWNTs soluble in water. The diameter-dependent reactivity selectively enhanced the water solubility of smaller diameter tubes, allowing for their separation by a competitive water-hexane partitioning method to divide the functionalized sample into different aqueous extracts of decreasing functionalization and solubility, yet also increasing diameter. The results were characterized with Raman spectroscopy which allowed the identification of diameter range characteristics of the functionalized SWNT fractions.

In a typical reaction, HiPco SWNTs (provided by Rice University, batch 112.1) were first purified using a $H_2O_2$/HCl one-pot purification method as previously reported (Wang et al., *J. Phys. Chem. B* 111:1249-1252 (2007)) to remove catalytic iron particles and amorphous carbon. The reaction began by efoliating 0.050 g (4.17 mmol of carbon) of the purified HiPco SWNTs in 75 mL liquid ammonia with the addition of sodium (0.14 g, 6.08 mmol). To the homogeneous dispersion was then added 6-bromohexanoic acid (1.625 g, 8.3 mmol) and the mixture was allowed to react for one hour. The nanotubes were repeatedly functionalized by alternately adding sodium and 6-bromohexanoic acid to the mixture to yield N-SWNT-$[(CH_2)_5COONa]_x$ (N indicates the number of reaction cycles). This recycling experimental protocol has allowed the functionalization SWNTs with ω-bromocarboxylic acids to produce water soluble nanotubes (up to 3,380 mg/L).

This progressive, functionalization chemistry shows a clear reactive preference for smaller diameter SWNTs as revealed by following the product using resonant Raman spectroscopy after each reaction cycle. The covalent addition of —$(CH_2)_5COOH$ onto the lattice of a SWNT depresses its characteristic Raman radial breathing mode (RBM, ~100-400 $cm^{-1}$) due to reduced tubular symmetry. The RBM peak frequency is inversely proportional to the corresponding SWNT diameter (Bachilo et al., *Science* 298:2361-2366 (2002). A clear diameter selectivity associated with the formation of N-SWNT-$[(CH_2)_5COONa]_x$ can be deduced from the Raman spectra. As shown in FIG. 1, the RBMs of the purified starting SWNT materials exhibit four typical peaks (198, 221, 258 and 285 $cm^{-1}$) in the resonance window of the 632.8 nm excitation line. As the reaction was repeated, the RBM peaks of the smaller diameter SWNTs (221, 258 and 285 $cm^{-1}$) decreased continuously and almost completely diminished after 20 cycles of reaction, when only the peaks at 198 and 221 $cm^{-1}$ were still observed. These trends suggest that the alkylcarboxylation of HiPco SWNTs prefers smaller diameter nanotubes. The diameter dependence was confirmed by the Raman results obtained with both 632.8 nm and 514.5 nm excitation. Since these two excitation lines are in resonance with metallic and semiconducting SWNTs of similar diameters respectively, the diminishing smaller diameter nanotubes in both excitation windows suggests this alkylcarboxylation reaction is not strongly inclined to a particular electronic type.

Without wishing to be bound by theory, this diameter-dependent alkylcarboxylation reaction can be attributed to diameter-dependent electron-transfer kinetics. In the Billups-Birch reaction, solvated electrons are involved in charge transfer to SWNTs. The reduction potential of $Na^+$/Na (in liquid ammonia) is −1.89V, lower than that of the largest semiconductor (Hersam, *Nature Nanotech.* 3:387-394 (2008) and Karousis et al., *Chem. Rev.* 110:5366-5397 (2010)) and metallic (Murakoshi and Okazaki, *Electrochimica Acta,* 50:3069-3075 (2005)) tubes within the HiPco diameter range (Nikolaev et al., *Chem. Phys. Lett.* 313:91-97 (1999)). Thus in the Billups-Birch reduction, CNTs act as an electron acceptor. The relative position of the Fermi level has been found to vary linearly with inverse nanotube diameter regardless of the electronic type (O'Connell et al., *Nature Mater.* 4:412-418 (2005)). Therefore, the difference in reduction potential between solvated electrons and smaller diameter/larger bandgap SWNTs is greater than that of larger diameter/small bandgap SWNTs. The smaller the diameter, the higher the reduction potential (Karousis et al., *Chem. Rev.* 110:5366-5397 (2010)). Thus it is not surprising that smaller diameter CNTs render more efficient reduction in the Billups-Birch reaction.

This diameter dependence is consistent with Wunderlich et al.'s observation for nanotube alkylation (Wunderlich et al., *J. Mater. Chem.* 18:1493-1497 (2008)), but the dependence is more substantial with the recycling alkylcarboxylation method described in this example. Importantly, alkylcarboxylation provides water solubility, allowing the separation of the functionalized nanotubes by diameter. Wet chemistry is an attractive approach to this difficult separation due to the prospect of high scalability. Diameter selective reactions by various functionalization methods, e.g., ozonolysis (Banerjee and Wong, *J. Phys. Chem. B* 106:12144-12151 (2002)) have been explored. However, successful separation is often limited due to the lack of solubility, scalability and the destructive nature of covalent methods. The current approach may overcome some of these limitations because 1) there is a strong diameter-dependent reactivity; 2) water solubility provides a means of physically separating SWNTs; 3) the Billups-Birch reaction is homogeneous which promises high scalability.

Figure 2:
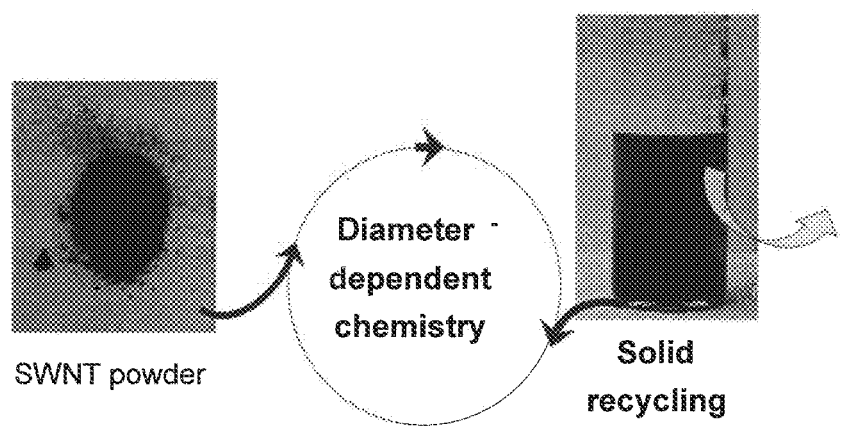
FIG. 2 is a scheme illustrating the solubility dependent water extraction of N-SWNT-$[(CH_2)_5COONa]_x$ via of progressive alkylcarboxylation extraction.
Figure 3:
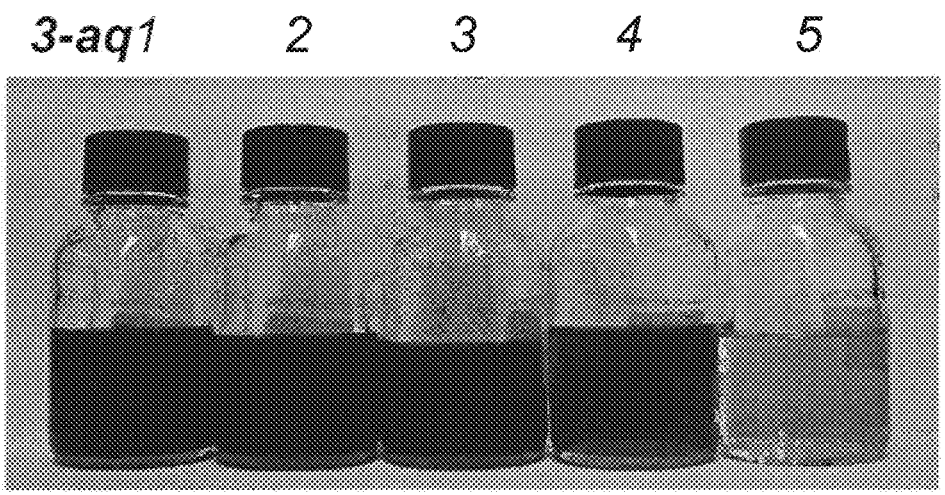
FIG. 3 is an image showing the water soluble fractions after three reaction cycles.

To investigate the prospect of this approach for diameter-dependent separation, a competitive solvation and partitioning technique was applied to separate functionalized SWNTs by solubility (Deng et al., *Chem. Commun.* 47:758-760 (2011)). This separation approach is depicted schematically in FIG. 2. The N-SWNT-$[(CH_2)_5COONa]_x$ were extracted with hexane by first re-dispersing the sample in 40 mL basic water (pH=10). The dispersion was transferred to a separatory funnel, to which 10 mL hexane was added and the mixture was shaken vigorously by hand. After phase separation, the black colored aqueous layer containing water soluble CNTs was collected, while the nanotubes remaining in the hexane layer were collected as a black solid by filtering the mixture over a Millipore TMTP membrane with 5 μm ion-etched pores. The dispersion and extraction process was repeated with the left-over solid (N-SWNT-$[(CH_2)_5COONa]_x$-leftover) until the aqueous layer became colorless or light colored, indicative of the separation of all the water soluble components. For sample 3-SWNT-$[(CH_2)_5COONa]_x$, four aqueous fractions, namely 3-aq(1-4), were obtained (FIG. 2). The amount of nanotubes solubilized in water was 20% of the total products. The insoluble residue was dried overnight in a vacuum oven at 80° C. and used as the starting material for an additional 3 alkylcarboxylation cycles (3,3-SWNT-[(CH$_2$)$_5$COONa]$_x$). A total of 11 soluble fractions, 3,3-aq(1-11), were collected by repeated hexane extraction which was 31% of the total product. The residual insoluble solid was further functionalized for 20 cycles to yield 3,3,20-SWNT-[(CH$_2$)$_5$COONa]$_x$, followed by the repeated extraction with hexane, from which a total of 5 water soluble fractions were obtained. These SWNT aqueous solutions are stable; no precipitation was observed, even after four months.

Figure 4:
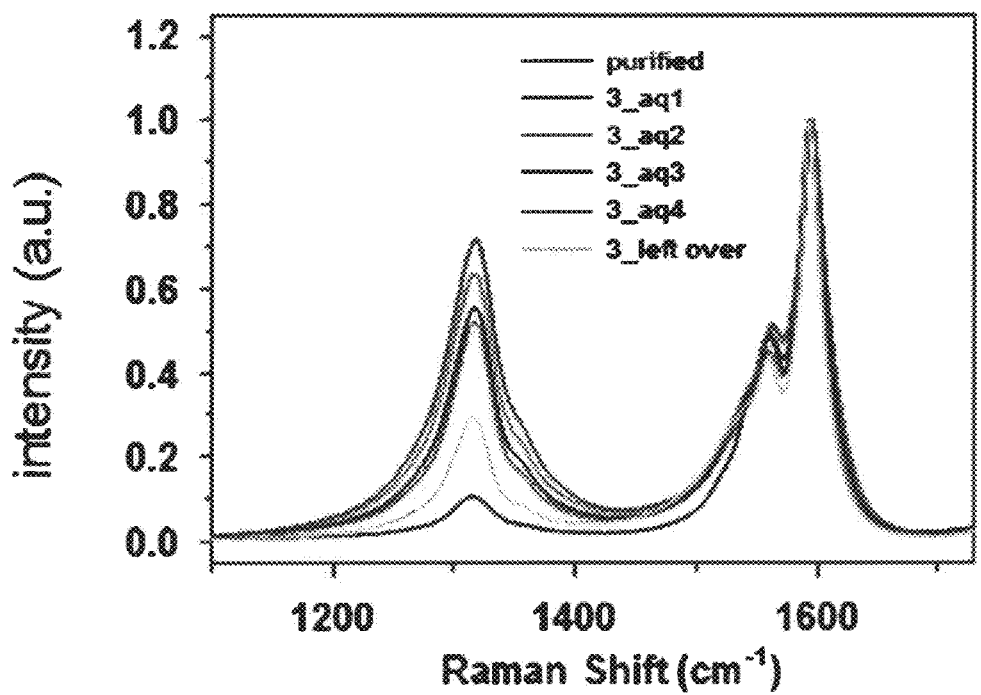
FIG. 4 is Raman spectra of water soluble fractions after 3 reaction cycles. The Raman excitation line is 632.8 nm.
Figure 5:
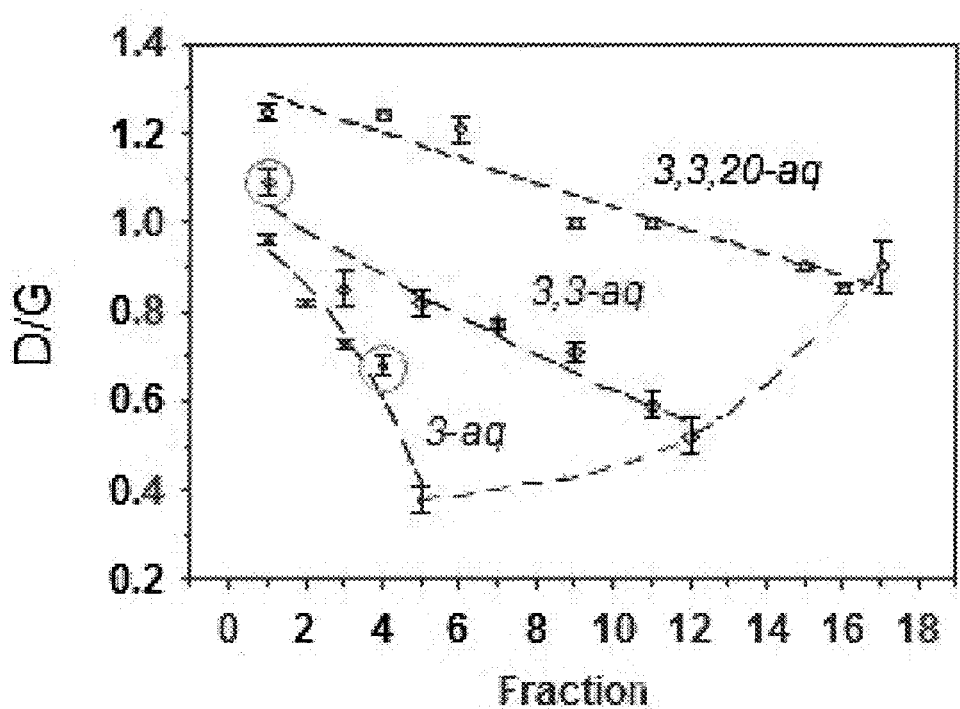
FIG. 5 is a line graph showing the evolution of Raman D/G peak area ratios for water soluble fractions after up to 3+3+20 reaction cycles. The Raman excitation line is 632.8 nm.

As shown in FIG. 4 and FIG. 5, the Raman integrated intensity of the D and G peaks ($I_D/I_G$), indicative of functionalization degree of the separated water soluble CNTs, was considerably higher than both the starting material and the residual, insoluble solid. The Raman $I_D/I_G$ of different fractions was inversely related to the order of extraction; the first extracted SWNTs exhibits the highest $I_D/I_G$ value. This trend persisted in every extraction experiment (FIG. 5). This is not surprising since water solubility is approximately proportional to the degree of alkylcarboxylation. Therefore, the extractions were driven by the degree of functionalization. As the extraction experiments were conducted, CNTs with different degrees of functionalization were sequentially obtained in each aqueous fraction. For example, the Raman $I_D/I_G$ varied from 1.09 to 0.59 for the CNT contents fractionalized from 3,3-SWNT-[(CH$_2$)$_5$COONa]$_x$.

Figure 6:
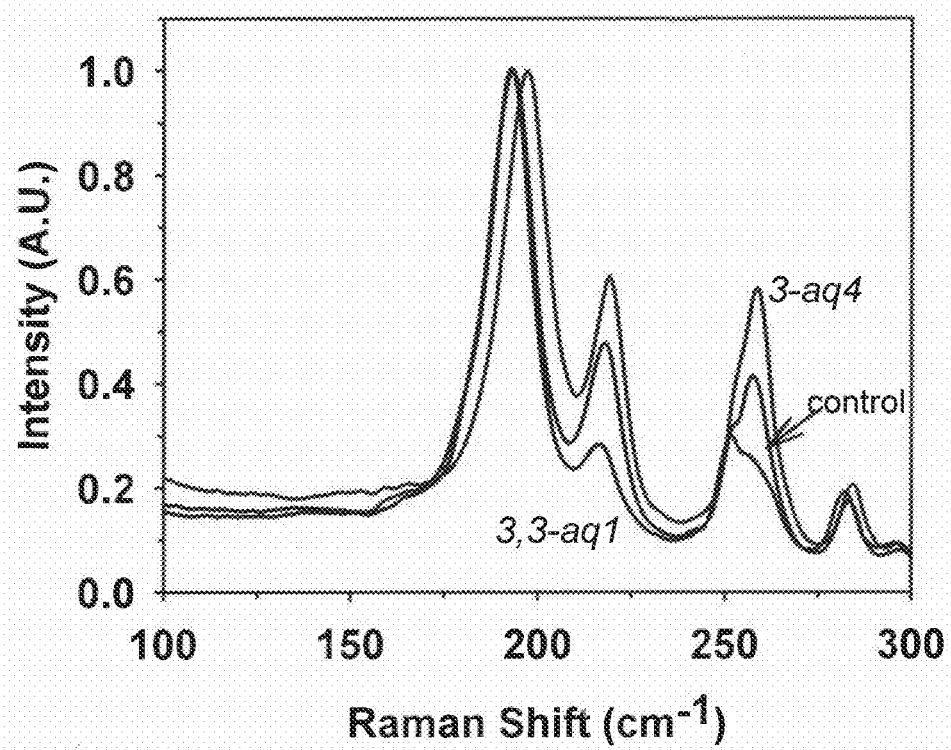
FIG. 6 is Raman spectra of CNT fractions in comparison with the starting material. The samples were annealed at identical conditions. The laser excitation line is 632.8 nm.

In order to confirm the diameter-dependent separation, the separated soluble fractions, 3-aq4 and 3,3-aq1, were thermally de-functionalized to recover tubular structure for Raman RBM assignment. Thermal annealing took place in a 25 mm diameter quartz tube furnace under flowing Ar/H$_2$. The temperature was raised to 100° C. and kept for 1 hour, followed by ramping at a rate of 20° C./min up to 600° C. The sample was kept at 600° C. for 1 hour and then allowed to cool to room temperature over 1.5 hours. FIG. 6 shows the RBM Raman spectra after thermal de-functionalization. For 3-aq4, the peak intensities at 221 and 258 cm$^{-1}$ increase; this suggests an enrichment of smaller diameter nanotubes in this fraction after annealing in comparison to the starting material. The next 3 cycles of functionalization were reacted with the remaining nanotubes in the 3-SWNT-[(CH$_2$)$_5$COONa]$_x$-leftover material which have larger diameters than the previously extracted aqueous fractions. Consequently, 3,3-aq1 had a higher content of larger diameter nanotubes as evidenced by the diminished RBM peaks at 221 and 258 cm$^{-1}$, indicative of smaller diameters (FIG. 6). These results confirm that the recycling alkylcarboxylation will selectively functionalize SWNTs in a manner that allows higher functionalized, more soluble, smaller diameter nanotubes to be extracted in earlier aqueous fractions with diameter distributions increasing for latter fractions. This type of selective partitioning of SWNTs by diameter enables a chemical approach to CNT separation.

Example 2

Diameter-Dependent, Progressive Alkylcarboxylation of SWNTs

A fundamental question of central importance to the development of selective chemistries for extended carbon networks, such as single-walled CNTs (SWNTs) (Karousis et al., *Chem. Rev.* 110:5366-5397 (2010)) and graphene (Allen et al., *Chem. Rev.* 110:132-145 (2010)), in which π-electrons are delocalized over thousands of carbon atoms, is where and how does a molecule covalently bond to a "π-electron sea." Theoretical studies predict that the pattern of functional groups, or defects, will substantially affect the electrical and optical properties of these types of low-dimensional systems (Garcia-Lastra et al., *Phys. Rev. Lett.* 101:236806 (2008); Lopez-Bezanilla et al., *Nano Lett.* 9:940-944 (2009)). Spatially controlled chemistry may find uses in graphene edge engineering (Sharma et al., *Nano Lett.* 10:398-405 (2010)), molecular lithography (Wang et al., *ACS Nano* 3:1049-1056 (2009)), and nanotube electrode networks (Brozena et al., *J. Am. Chem. Soc.* 132:3932-3938 (2010)). Experimentally, it is challenging to control functionalization patterns in carbon nanostructures. Recent experiments have demonstrated that diazonium chemistry and oxidative reactions occur on a SWNT sidewall at completely random atomic sites (Goldsmith et al., *Science* 315:77-81 (2007); Cognet et al., *Science* 316:1465-1468 (2007)). The covalent modification of even a single site results in a substantial drop of electrical conductance (Goldsmith et al., *Science* 315:77-81 (2007)) and stepwise quenching of exciton fluorescence in semiconducting nanotubes (Cognet et al., *Science* 316:1465-1468 (2007)).

Figure 7:
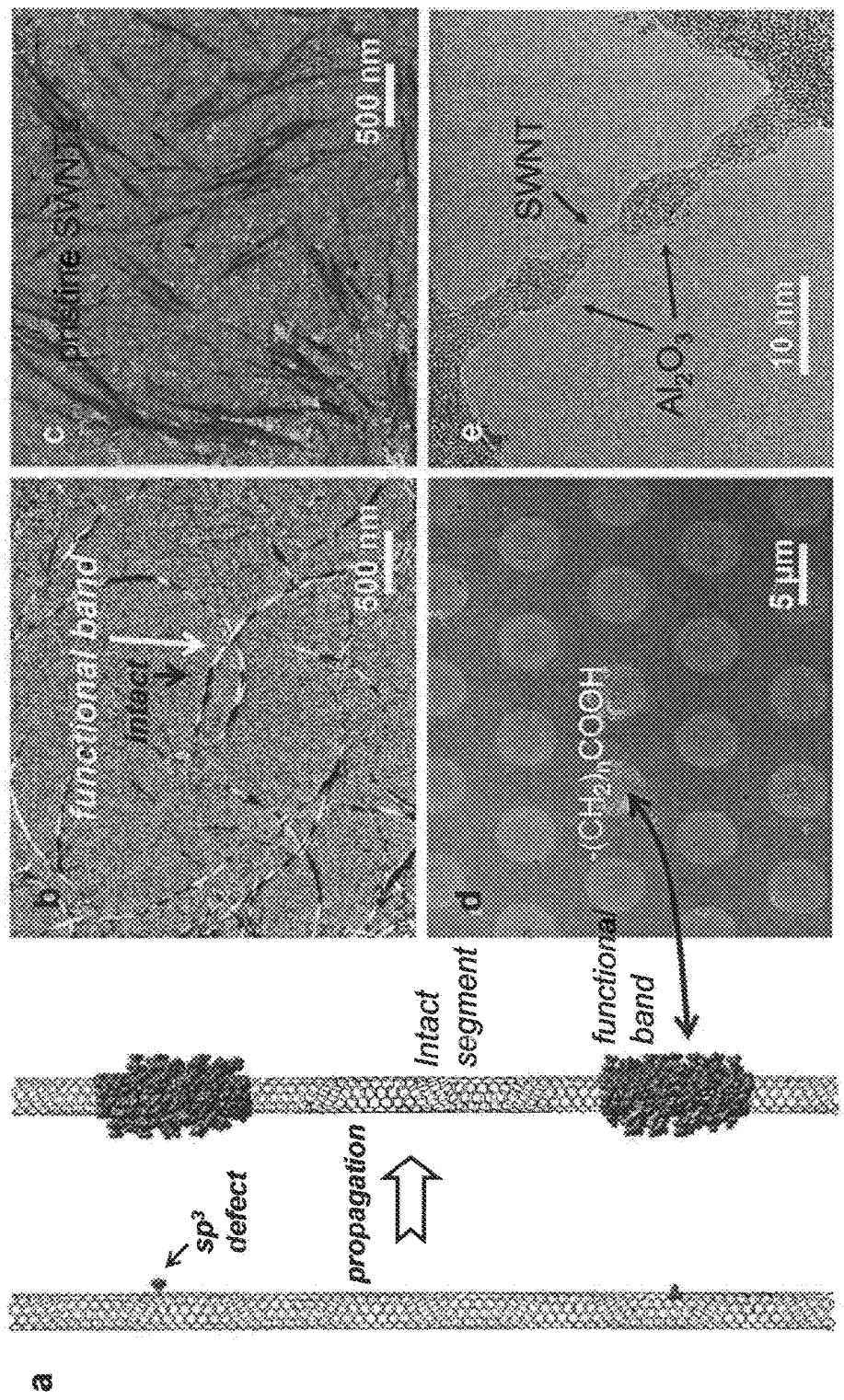
FIG. 7 is a schematic illustration and a series of four images showing functional bands on SWNTs: (a) Schematic illustration of reaction propagation initiated at $sp^3$ defect centers that ultimately propagate along the tubular direction, creating $sp^3$ bands of functional groups: (b) Alkylcarboxylated nanotubes on a gold substrate imaged using a scanning electron microscope operated at 1 kV. The dark and, bright contrasts closely resemble pristine nanotubes (c) and patterned carboxylic acids (d), respectively; and (e) High resolution transmission electron microscopy image of an individual SWNT-$[(CH_2)_5COOH]_n$ coated with $Al_2O_3$ by —COOH selective atomic layer deposition using trimethyl aluminum and $H_2O$ precursors.
Figure 14:
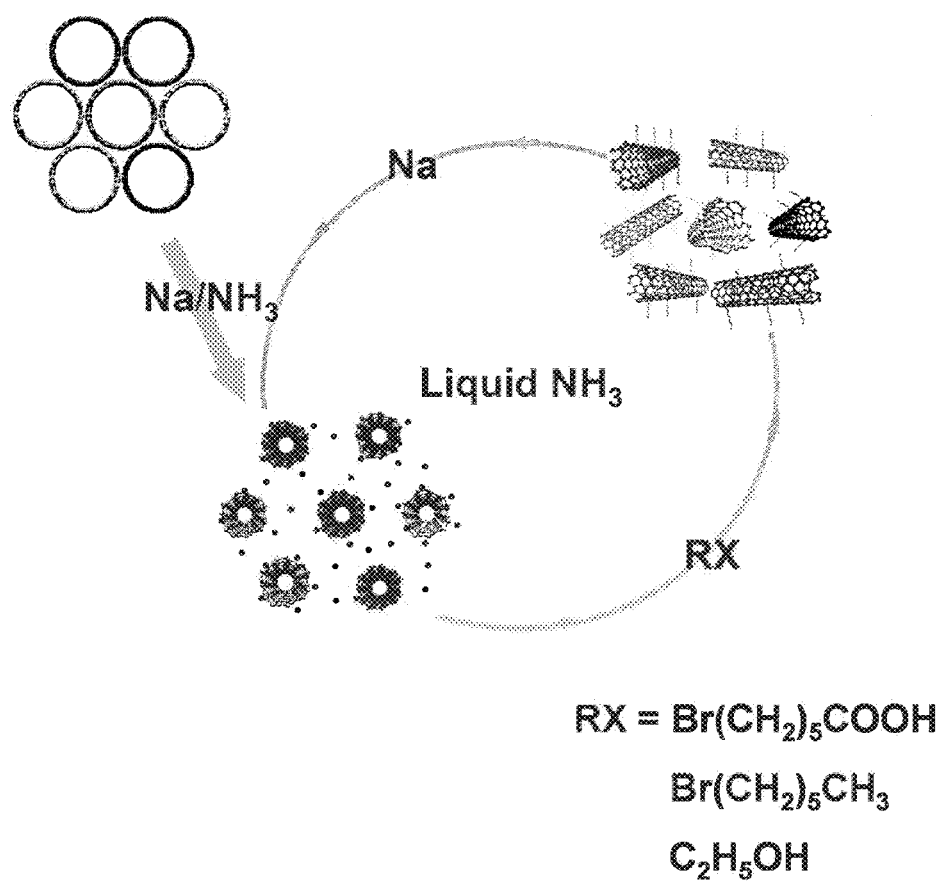
FIG. 14 is a schematic illustration of the recycling and reductive alkylation reaction (with the alkylating agent RX) of SWNTs.

In this example it is shown that the Billups-Birch reductive alkylcarboxylation (Deng et al., *Chem. Comm.* 47:758-760 (2011)), a variant of Birch reduction chemistry (Liang et al., *Nano Lett.* 4:1257-1260 (2004); Birch, *J. Chem. Soc.* 430-436 (1944)), occurs on SWNTs exclusively, to the extent observable in this example, by reaction propagation from existing defects—the edge of the π-electron sea. CNTs were homogenously dispersed in an ammonia solution of solvated electrons and covalently functionalized by alternating addition of sodium and various alkyl-halide reagents in a recycling procedure (FIG. 14). The propagation mechanism of this chemistry makes it possible to progressively add new functional groups to the graphene lattice without nucleating unintended new defects. This defect-activated chemistry bears a remarkable analogy to the high reactivity of nanotube ends (Chen et al., *Science* 282:95-98 (1998); Ziegler et al., *J. Am. Chem. Soc.* 127:1541-1547 (2005)) and step edges in surface science (Rublof et al., *Phys. Rev. Lett.* 58:2379-2382 (1987); Chung et al., *Phys. Rev. Lett.* 97:036103 (2006)). Confinement of the reaction to CNT "sp$^3$ step edges" leads to reaction fronts initiated at defect sites that ultimately propagate along the tubular direction at a constant rate (FIG. 7a).

"Banded" SWNTs: The sp$^3$ defect propagation mechanism was most directly illustrated by the creation of "banded" SWNTs, with alternating segments of functionalized (sp$^3$ hybridized) and intact regions (which remain sp$^2$ hybridized) through reaction propagation that starts at defects initially present in the nanotubes or introduced during the H$_2$O$_2$/HCl purification process (Wang et al., *J. Phys. Chem. B* 111:1249-1252 (2007)). The functionalized and intact regions along the same nanotube were simultaneously resolved by substrate-enhanced scanning electron microscopy (Zhang et al., *J. Phys. Chem. Lett.* 2:885-888 (2011)). When such functionalized nanotubes were deposited on a gold substrate and imaged with an SEM electron beam of 1 kV, regular alternation of bright and dark contrast along the nanotube length were observed (FIG. 7b). The sharp image contrast arises from a substantial increase in the yield of secondary electrons at 1 kV due to covalent modification of the nanotube. After annealing the samples at 750° C. under flowing Ar/H$_2$ for one hour, which fully recovered the pristine structure of the nanotubes, the banding structures were lost and the images show the same contrast as those of raw nanotubes (FIG. 7c). The brighter regions exhibit a contrast comparable to those of microcontact-printed 16-mercaptohexadecanonic acid on a gold substrate (FIG. 7d). Based on these observations the bright contrast can be unambiguously attributed to alkylcarboxylic acid groups and the darker regions to intact nanotubes.

Notably, this propagation mechanism persists even after extensive reaction. With the aid of atomic layer deposition (ALD), small segments of intact nanotubes (5-10 nm) were still frequently observed after repeating the covalent functionalization reaction 40 times. FIG. 7e shows a TEM image of an individual SWNT where $Al_2O_3$ was selectively grown on the carboxylic acid functional groups by alternately pulsing trimethyl aluminum and $H_2O$ at 150° C. Because this ALD chemistry is self-limiting and chemically selective to reactive functional groups (here carboxylic acids) (Leskela, and Ritala, *Angew. Chem. Int. Ed* 42:5548-5554 (2003); Farmer and Gordon, *Electrochem. Solid-State Lett.* 8:G89-G91 (2005); Wang et al, *J. Am. Chem. Soc.* 130:8152-8153 (2008)) the discrete $Al_2O_3$ coating reflects the clustered distribution of the functional groups, —$(CH_2)_5COOH$, along the nanotube.

Figure 8:
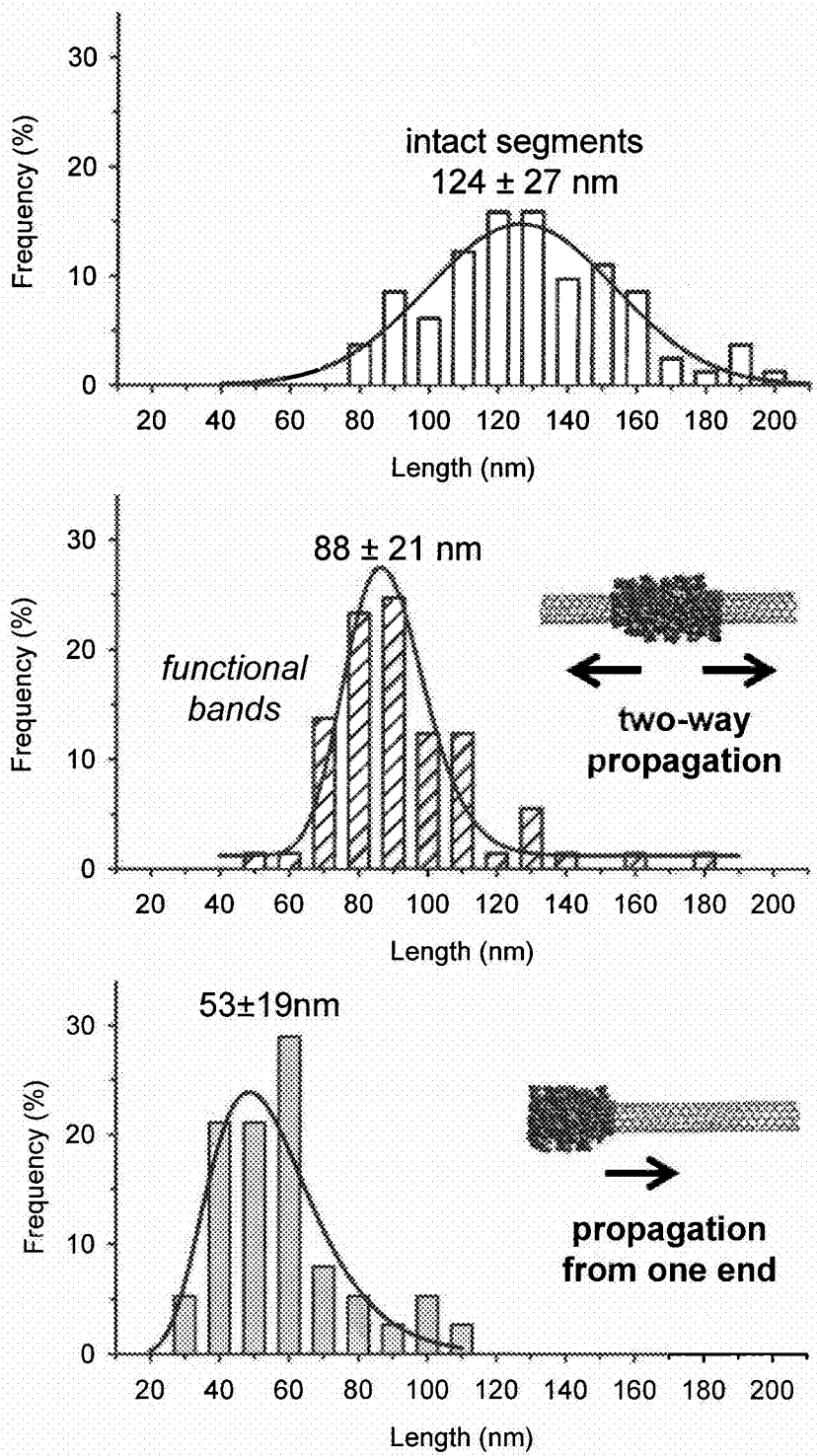
FIG. 8 is a series of three bar graphs showing the two modes of propagation revealed in the length distributions of intact segments and functional bands. The lengths were extracted from scanning electron microscopy images of the same alkylcarboxylated nanotube sample. The sample sizes are 82, 73, and 38, respectively. The curves were fitted in Gaussian, log-normal, and log-normal functions with peaks at 124±27, 88±21, and 53±19 nm, respectively. The errors are standard deviations.

Propagation modes: Two distinct modes of defect propagation were revealed in the length distribution of the SEM-resolved intact segments and functional bands (FIG. 8). The intact segments (124±27 nm in length) follow a broad, Gaussian length distribution, suggesting a random spatial distribution of initial defects on the pristine nanotubes, as expected, at an average pitch of 212±48 nm (lower bound limit since two or more defects in proximity can develop a merged functional band). This low defect density is corroborated with negligible weight loss at elevated temperatures due to decomposition of the functional groups, low disorder peak in Raman spectra, and bright fluorescence from individually dispersed pristine nanotubes. In contrast to the intact segments, the functional bands have much narrower distributions. More than 80% of the 81 nanotube ends identified by SEM imaging had a functional band. These end functional bands extend 53±19 nm on average after three reaction cycles, which is approximately half the length of bands located along the nanotube sidewall (88±21 nm) (FIG. 8). This strong length correlation arises because a defect on the nanotube sidewall will allow the propagation to occur in both directions equally, while there is only one possible direction to propagate from a SWNT end, the natural defect in the π-electron sea. Note that a reaction cycle in the reductive alkylcarboxylation is limited by the reductant (solvated electrons) which can be stored in the nanotube before reaction.

Figure 9:
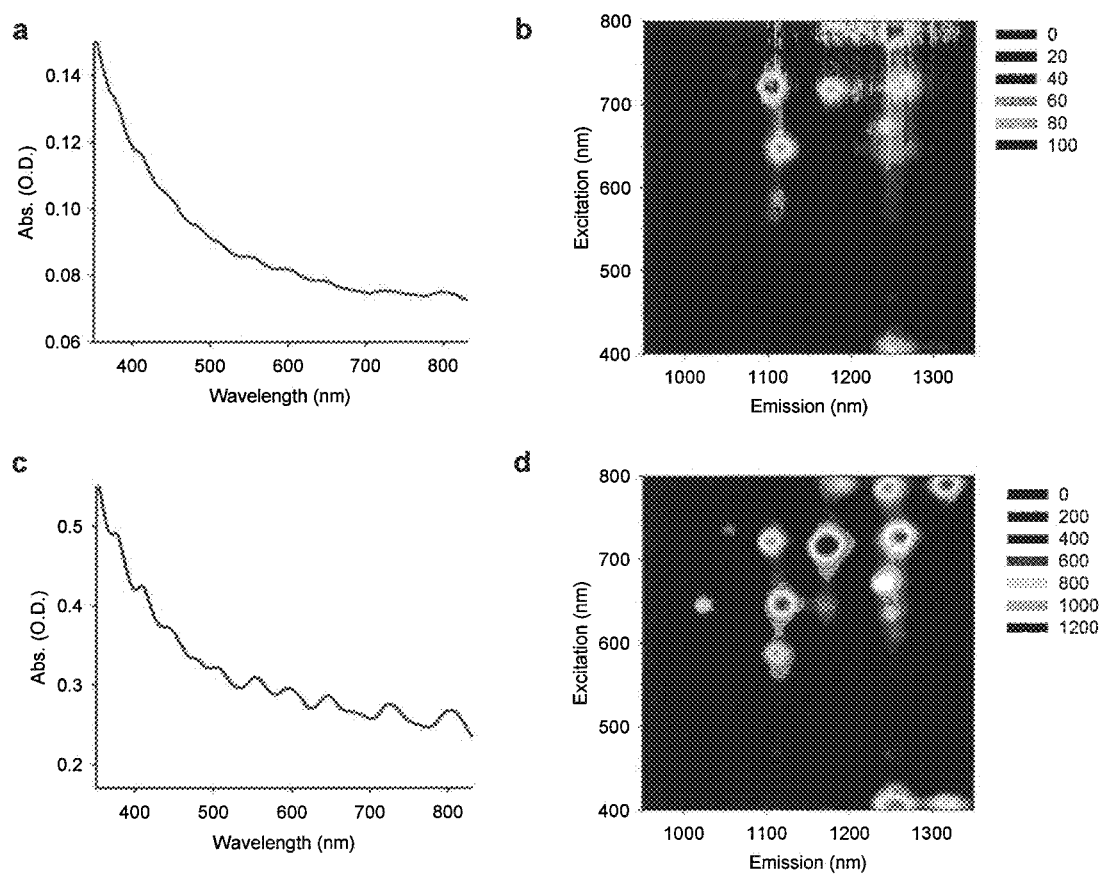
FIG. 9 is two ling graphs and two images showing the optical properties of functionalized and unfunctionalized CNTs: (a) Visible-NIR absorption spectrum; and (b) Excitation-emission map of 3-cycle HiPco-SWNT-$[(C_2H_5)_5COOH]_n$ in comparison with (c,d) the starting, unfunctionalized nanotubes, which were individually dispersed in $D_2O$ solutions of 1% sodium dodecylbenzenesulfonate.
Figure 15:
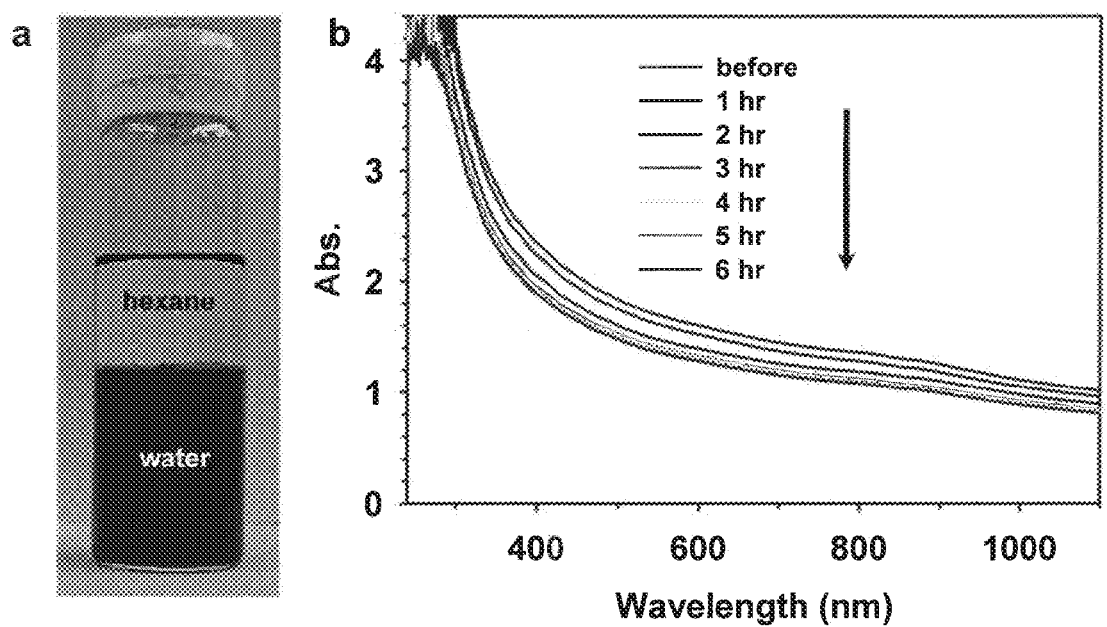
FIG. 15 is an image and UV-VIS-NIR spectra showing water soluble SWNT-[(CH$_2$)$_5$COONa]$_n$: (a) Under solvation competition between water and hexane; and (b) Determination of water solubility of nanotubes by optical-centrifugation. UV-VIS-NIR spectra of 20-cycle-functionalized HiPco-[(CH$_2$)$_5$COONa]$_n$ before and after centrifugation at 5100 rpm (1919 g). The saturated nanotube solution was diluted 10 times before the centrifugation.

Optical properties: The covalently functionalized SWNTs retained some of the optical properties of SWNTs (FIG. 9). Optical properties of nanotubes are often completely lost due to covalent modification of the electronic band structures by even a small number of defects (Cognet et al., *Science* 316:1465-1468 (2007); Strano et al., *Science* 301:1519-1522 (2003)). A defect density of ~1/10,000 (~0.001%) is sufficient to completely quench nanotube fluorescence (Cognet et al., *Science* 316:1465-1468 (2007)). Partial retention of the van Hove optical absorption (Strano et al., *Science* 301:1519-1522 (2003)) and exciton fluorescence (Cognet et al., *Science* 316:1465-1468 (2007)) properties was made possible here even at a high degree of functionalization (~45 functional groups per 1000 carbons) because of clustered distribution of the —$(CH_2)_5COOH$ functional groups along the nanotube length, leaving intact regions of $sp^2$ hybridized carbons with sustained band structures (FIG. 7a,b). This propagation chemistry has allowed the production water soluble nanotubes (up to 3,380 mg/L) after 40 cycles of reaction (FIG. 15). This high water solubility was previously unexpected (Davis et al. *Nat. Nanotechnol.* 4:830-834 (2009); Chattopadhyay et al, *Chem. Mater.* 18:5864-5868 (2006); Moniruzzaman et al., *Nano Lett.* 7:1178-1185 (2007)).

Figure 10:
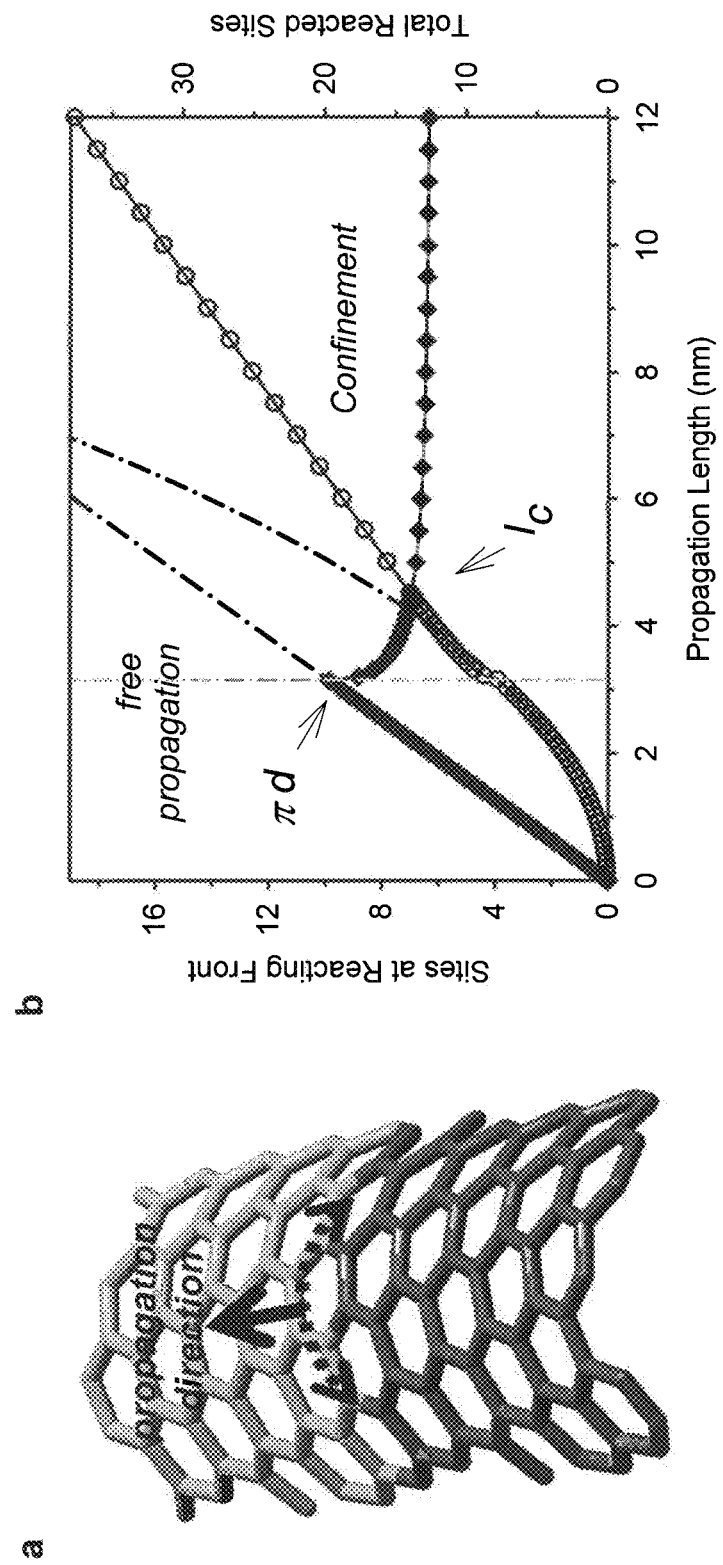
FIG. 10 is a schematic illustration of the propagation front and a line graph supporting a kinetic model of reaction propagation from a point defect on a $sp^2$-bonded carbon lattice of a CNT: (a) Schematic of the propagation front. For clarity the functional groups are omitted. Note that for most chemistry only a small fraction of carbon sites within the functional band are functionalized; and (b) Propagation with confinement to the nanotube cylinder (solid lines) vs. free propagation on an infinite sheet (dotted lines). The sites at the reaction front (diamond) and total reacted sites (open circles) are computed based on geometry considerations for a 1 nm diameter nanotube. For the defect-activated reaction, the reaction rate is proportional to the number of $sp^3$ defect centers available at the reaction front, which initially increases linearly with propagation length. At a higher degree of functionalization, specifically when the propagation length reaches the circumference of the nanotube $\pi d$, the reaction propagation becomes confined to the tubular direction. The degrees of freedom for propagation along the nanotube circumference are completely lost at a critical propagation length $l_c$, ~1.5$\pi d$, after which the reaction rate becomes a constant.

Without wishing to be bound by theory, a simple kinetic model can account for the observed propagation of functional bands (FIG. 10). For free propagation from a point defect without any constraint, the number of reaction sites at the reaction front will continuously accelerate as the "$sp^3$ step edge" expands. A transition occurs at a propagation length equal to the circumference of the nanotube, and then at which point propagation becomes confined in a banded morphology down the length of the tube. The reaction rate becomes constant after the propagation reaches a critical length, $l_c \sim 1.5 \pi d$, where d is the nanotube diameter—the ultimate limit of the $sp^3$ step edge. For a 1 nm diameter SWNT, this simple model shows that the propagation becomes confined as the reaction expands beyond approximately 5 nm from a defect center. From the nanotube end functional bands, the propagation rate is estimated to be 18±6 nm per reaction cycle under the experimental conditions investigated.

To more quantitatively describe this picture of reaction propagation, the relative probability of propagation with respect to the spatially random addition of new functional groups (nucleation) was calculated. This parameter defines the "purity" of reaction propagation. This parameter can be experimentally determined by estimating the lower limit number of functional groups within a functional band compared to random nucleation, if any, in the intact segments as reflected by fluorescence. For the SEM-resolved bands of a 3-cycle carboxylic acid functionalized sample (FIG. 8), the corresponding average functional density, or the percentage of nanotube carbon atoms that are covalently functionalized, was ~4.5% based on the weight loss of functional groups at elevated temperatures under argon by thermogravimetric analysis (TGA). Given average lengths of 88 and 124 nm functionalized and intact regions respectively, the functional density within the band can be calculated as at least 12%, suggesting only a fraction of the carbons within the band were functionalized. As such, an 88 nm band contains more than 1300 functional groups on average for a 1 nm diameter CNT. At this degree of functionalization, the nanotubes fluoresced with a relative quantum yield 25% that of the initial starting nanotubes (FIG. 9). Since a single defect can quench the exciton fluorescence as it diffuses rapidly over 90 nm during its lifetime (Cognet et al., *Science* 316:1465-1468 (2007)), no more than 1 random nucleation on average should have occurred within the intact segments (124±27 nm). Taken together, the relative probability of propagative functionalization is at least 1300 times higher than random nucleation. This spatial selectivity is more than 600 times higher than diazonium chemistry, the only other covalent addition chemistry whose spatial selectivity on carbon is quantified (Sharma et al., *Nano Lett.* 10:398-405 (2010)). It is important to note that banding has been observed previously with scanning tunneling microscopy on fluorinated nanotubes (Kelly et al., *Chem. Phys. Lett.* 313:445-450 (1999)), but the fluorination bands are densely spaced (pitch<10 nm vs. the observed ~210 nm in this example), suggesting substantial contamination by random nucleation even if fluorination chemistry partially follows the propagation mechanism proposed here.

Figure 16:
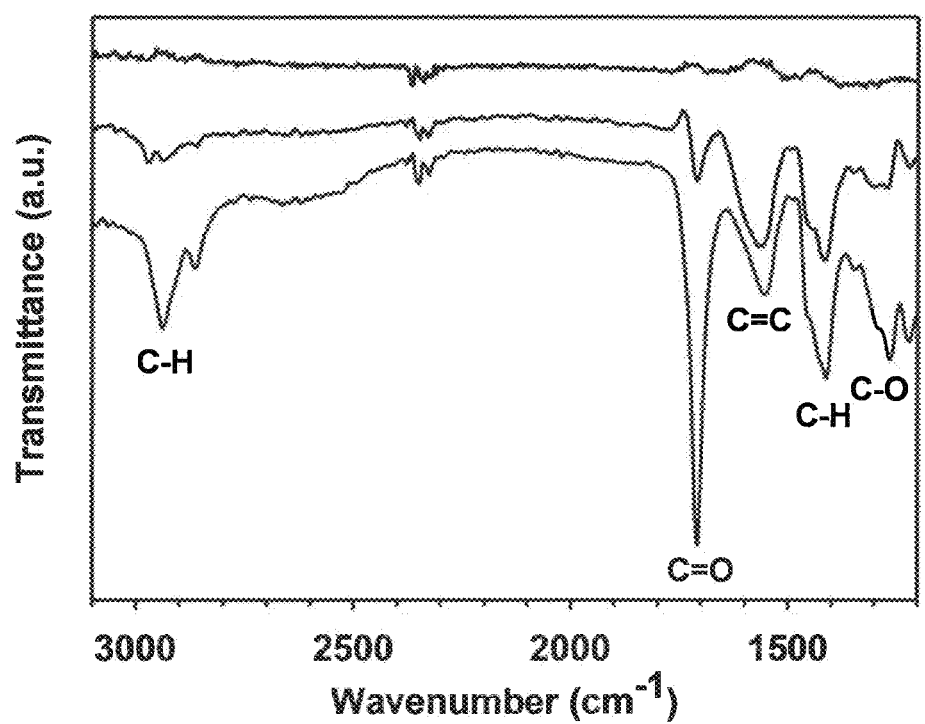
FIG. 16 is a FT-IR of SWNT-[(CH$_2$)$_5$COOH]$_n$ showing increased IR absorbance for —COOH and C—H from starting HiPco material (top curve), after 1 cycle functionalization (middle curve) and 33 cycles of functionalization (bottom curve).

To gain further insight, the reaction was repeated up to 40 cycles on CoMoCat (6,5) SWNTs and characterized the functionalized nanotubes with correlated TGA, Raman spectroscopy, FT-IR, and water solubility measurements (FIG. 11, FIG. 15, FIG. 16, and FIG. 17). The FT-IR spectra unambiguously confirmed the rise of various IR peaks after functionalization that are characteristic of C—H (2800-3000 $cm^{-1}$, C—H stretch; 1415 $cm^{-1}$, C—H bending) and —COOH moieties (1709 cm$^{-1}$, C=O stretch; 1260 cm$^{-1}$, C—O stretch). The C=O stretching mode grew consistently with increasing degrees of functionalization, in stark contrast with the featureless IR spectrum of the pristine SWNT control (FIG. 16). Consistently, the functional density grew linearly at increasing reaction cycle, as predicted by the confined propagation model (FIG. 11b).

Figure 11:
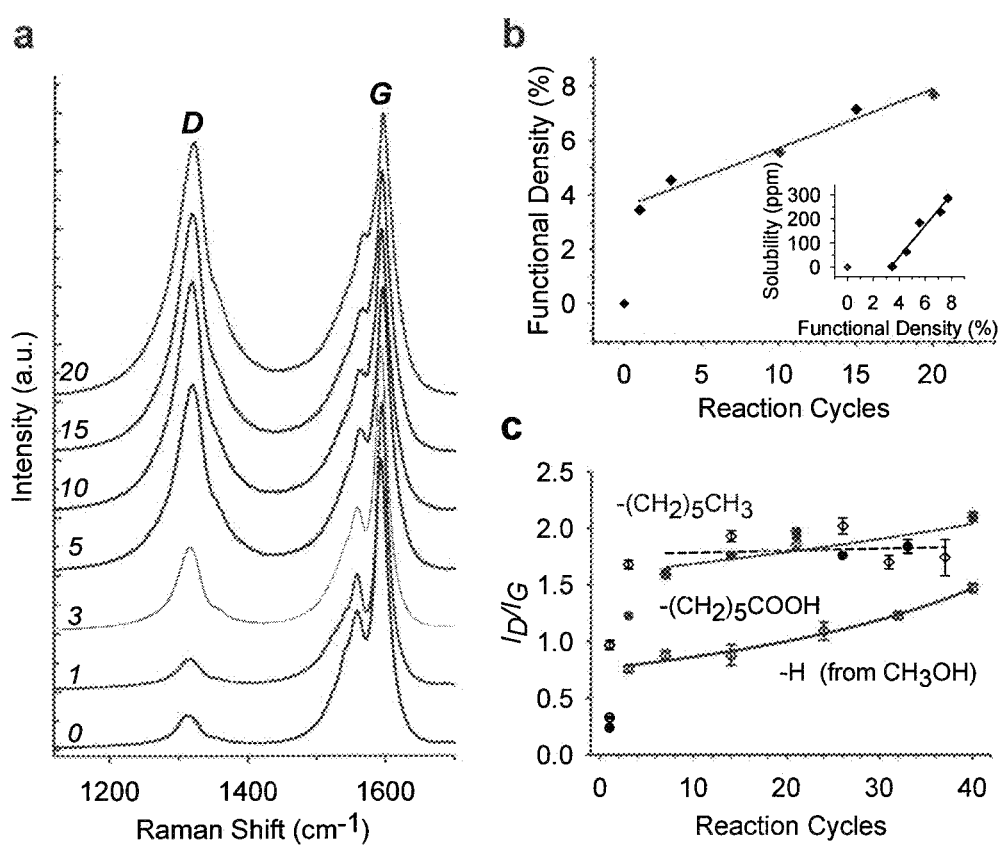
FIG. 11 is Raman spectra and two line graphs showing the evolution of Billups-Birch reductive addition: Correlated (a) Raman spectra, (b) degree of functionalization as determined from weight loss in thermogravimetric analysis (TGA), and water solubility (b, inset) as a function of reaction cycles for a HiPco SWNT sample after 0 to 20 cycles of functionalization with $Br(CH_2)_5COOH$. The excitation line is 632.8 nm. The degree of functionalization increased as a linear function of reaction cycles. The functionalized nanotubes became water soluble at a threshold functional density of approximately 3.5% and thereafter increased linearly as a function of reaction cycle; and (c) Effect of terminating groups on the reaction propagation probed with Raman spectroscopy. (6,5) enriched CoMoCat SWNTs were used for this study. The data were fitted by a rational function in the form $$y = \frac{D + ax}{G - bx}.$$

This reaction propagation mechanism is true of other functional groups as well. For all three groups investigated, including —(CH$_2$)$_5$CH$_3$, —(CH$_2$)$_5$COOH, and —H, Raman spectroscopy revealed similar trends of reaction propagation (FIG. 11) and similar banding structures were found by SEM (except —H) (Zhang et al., *J. Phys. Chem. Lett.* 2:885-888 (2011)). Covalent sidewall chemistry introduces sp$^3$ defect centers, which decrease the Raman oscillator strength of the tangential modes around 1450-1650 cm$^{-1}$ (G bands) and give rise to the so-called D band (around 1350 cm$^{-1}$) (Dresselhaus et al., *J. Phys. Chem. C* 111:17887-17893 (2007)). This allowed the use of the D/G ratio (peak area ratio between the D-band and the G-bands) to follow the reaction progress (FIG. 11c). For the first 3-5 cycles of reaction, the D/G ratio rose exponentially, corresponding to the initial propagation from the sp$^3$ defect sites which quickly convert a long nanotube into shorter segments from the Raman perspective. This is consistent with previous observations from length sorted SWNTs that the D/G ratio rises inversely as a function of nanotube length (Chou et al., *Appl. Phys. Lett.* 90:131109 (2007); Simpson et al., *Carbon* 47:3238-3241 (2009)). However, as the reaction continued, the trend follows a simple form, $$\frac{D}{G} = \frac{D_0 + ax}{G_0 - bx}.$$

This trend reflects a constant growth of the number of defects (x), which contribute to the increase of the D-band (D) and simultaneous decrease of the G-band (G) intensity at relatively constant weights (a/b), a feature made uniquely possible by the confined propagation.

Figure 12:
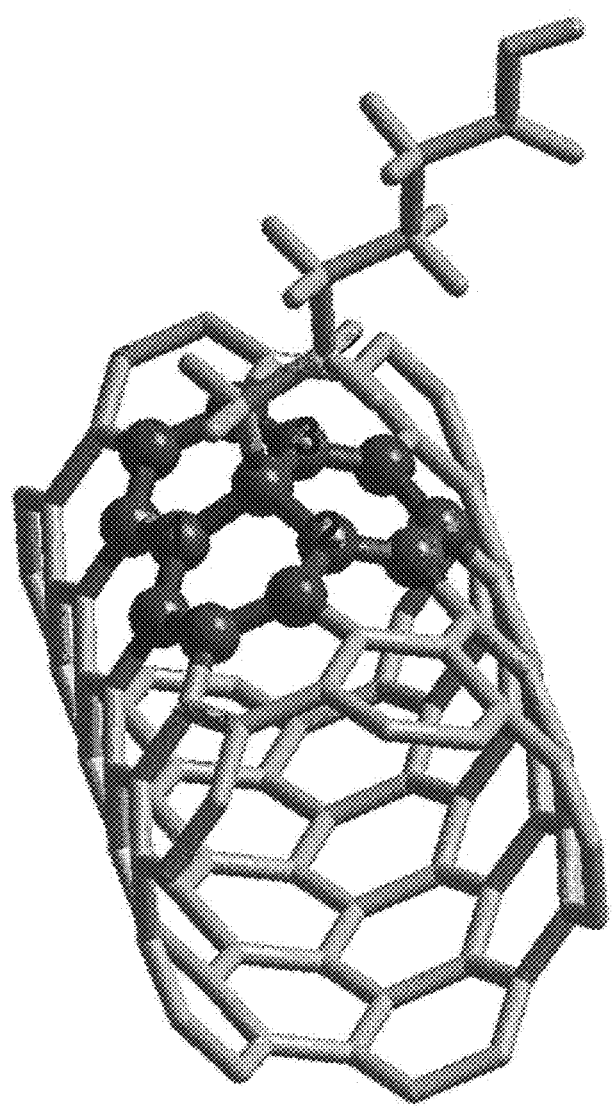
FIG. 12 is an illustration showing the optimized structure of a (5,5)-SWNT with a covalently bonded —$(C_2H_5)_5COOH$ group. The added electrons are largely localized on the highlighted carbon atoms.
Figure 13:
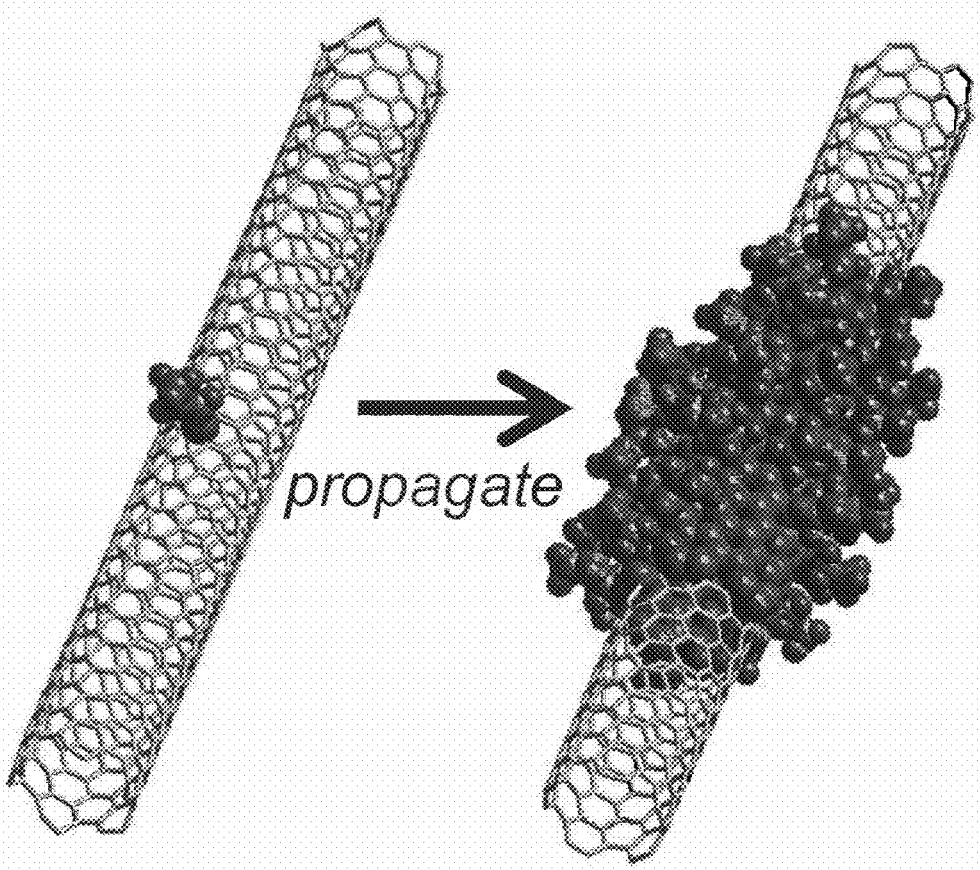
FIG. 13 is a schematic illustration showing that covalent functionalization propagates in vicinity of a single point defect on the $sp^2$-bonded carbon lattice on the nanotube into band morphology.

The initial defect density is extremely low, approximately 1/10,000 (the fluorescence limit) (Cognet et al., *Science* 316:1465-1468 (2007)) to 1/30,000 (average pitch of functional bands). However, the observed progressive alkylcarboxylation of nanotubes over at least tens of nanometers suggests that these functional groups can act as new defect centers for continued propagation of the reaction fronts. To simulate the electronic effects of a single sp$^3$ defect, density functional theory (DFT) calculations were performed on —(CH$_2$)$_5$COOH group functionalized (5,5)-SWNT (FIG. 12) and (10,0)-SWNT using periodic boundary conditions. The generalized gradient approximation (GGA) of the Perdew-Burke-Ernzerhof (PBE) functional, a double-ζ basis set, and the standard norm-conserving Troullier-Martins pseudopotentials was used (Troullier and Martins, *Phys. Rev. B: Condens. Matter* 43:1993-2006 (1991)). A Mulliken population analysis shows that the charges are localized in the carbons around the sp$^3$ defect and the remaining atoms have very little, almost negligible, charges (Table 1). When more electrons are added to the nanotube, as in the Birch reduction, the most significant charges are trapped around the defect site. This electronic effect extends as much as another C—C bond beyond the rings to which the functional group is attached. These results suggest that the observed propagation phenomenon originates from two effects: (1) electrons are trapped around the defects; and (2) the trapped electrons promote localized Birch reductive addition. These are essentially the same rules that govern the regioselectivity of the Birch reduction in small aromatic compounds such as anisole (Zimmerman and Wang, *J. Am. Chem. Soc.* 115:2205-2216 (1993)). In an electron-delocalized system as large as a CNT, the Birch reduction occurs by propagating the reaction fronts at the edge of the electron sea.

TABLE 1

Net atomic charges around a sp$^3$ defect site from Mulliken population analysis of a SWNT with a covalently bonded —(CH$_2$)$_5$COOH group.

|  | neutral | −1 charge | −2 charge |
| --- | --- | --- | --- |
| (5,5)-(CH$_2$)$_5$COOH |  |  |  |
| defect site | 0.12 | 0.13 | 0.13 |
| C1 | −0.04 | −0.07 | −0.08 |
| C2 | −0.02 | −0.05 | −0.06 |
| C3 | −0.02 | −0.05 | −0.06 |
| (10,0)-(CH$_2$)$_5$COOH |  |  |  |
| defect site | 0.12 | 0.13 | 0.13 |
| C1 | −0.04 | −0.06 | −0.07 |
| C2 | −0.01 | −0.02 | −0.02 |
| C3 | −0.04 | −0.06 | −0.07 |

* Carbon atoms not listed have a charge close to zero, being as high as −0.01 e, and −0.02 e charges for neutral, −1, and −2 CNTs.

Materials: Two SWNT materials, HiPco (Rice University) and (6,5)-enriched CoMoCat (Southwest Nanotechnologies, Inc.), were used in this study. HiPco SWNTs were purified using a one-pot purification method (Wang et al., *J. Phys. Chem. B* 111:1249-1252 (2007)) and CoMoCat SWNTs were used as received. All other reagents were purchased from Sigma-Aldrich and used without further purification.

Synthesis of HiPco-[(CH$_2$)$_5$COONa]$_n$: In a typical experiment, purified HiPco SWNTs (10 mg, 0.83 mmol of carbon) were added to a flame-dried, argon purged, 250 mL four neck round-bottom flask fitted with a dry-ice/acetone condenser. 75 mL liquid ammonia was condensed into the flask followed by addition of sodium (0.029 g, 1.25 mmol), which spontaneously produced a blue color owing to solvated electrons. After stirring for 10 minutes, 6-bromohexanoic acid (0.975 g, 5.00 mmol) was added and the mixture was stirred overnight while the liquid ammonia evaporated. Subsequently, 100 mL nanopure water was added to the flask and briefly sonicated. The functionalized SWNTs were collected over a 0.8 μm ATTP membrane (Millipore), re-dispersed in water and repeatedly extracted with hexane (20 mL) in a separatory funnel to remove salts. The hexane layer was filtered through a 0.8 μm membrane forming a buckypaper of functionalized SWNTs, which was washed with ethanol and water and dried overnight in a vacuum oven at approximately 80° C.

For multiple reaction cycles, the previously functionalized SWNTs were used as starting materials. Sodium and 6-bromohexanoic acid were alternately added into the flask at each reaction cycle (FIG. 14). After the first cycle: extra sodium was added to balance the loss due to the reactive —COOH groups. For each cycle, the solution was allowed to react for one hour.

Synthesis of CoMoCat-[(CH$_2$)$_5$COONa]$_n$, CoMoCat-[(CH$_2$)$_5$CH$_3$]$_n$ and CoMoCat-[H]$_n$: CoMoCat SWNTs (20 mg, 1.67 mmol) were exfoliated in 75 mL liquid NH$_3$ by sodium (0.058 g, 2.5 mmol), and subsequently reacted with 6-bromohexanoic acid (0.650 g, 3.33 mmol), 1-iodohexane (0.706 g, 3.33 mmol), or methanol (0.533 g, 16.67 mmol). Up to 40 reaction cycles were carried out using the same procedures as described above.

3-Cycle reaction and water extraction: Water extraction experiments were carried out on 3-cycle functionalized HiPco-[(CH$_2$)$_5$COONa]$_n$ sample, beginning with 52 mg purified HiPco-SWNTs. After functionalization, the black solid was dispersed in 80 mL basic water (pH=10.5). 10 mL hexane was then added to the dispersion and the mixture was shaken vigorously. After phase separation, the aqueous phase was collected. The hexane layer of SWNTs was filtered over 0.2 µm GTTP Isopore membrane (Millipore). This extraction process was repeated to produce 13 bottles of water soluble SWNT solutions, the last third of which exhibited the optical properties as shown in FIG. 9.

Solubility Measurement:

The water solubility was measured by centrifugation in conjunction with UV-Vis-NIR spectroscopy. The solid samples were dispersed in basic water (pH=10) by bath sonication for 1 hour. Then the aqueous solutions were centrifuged on a Beckman Coulter Microfuge 16 centrifuge (Brea, Calif.) at 1919 g until the supernatant reached a stable, isotropic phase showing no further decrease in absorbance (FIG. 15).

Spectroscopy characterization: Raman scattering spectra were collected on a Horiba Jobin-Yvon LabRAM HR-VIS microRaman system with a helium neon laser excitation source. Lower power density (~0.1 mW/µm$^2$) was used to exclude laser induced thermal effects (Zhang et al., *J. Phys. Chem. C* 111:1988-1992 (2007)). UV-Vis-NIR spectra were measured using a Perkin Elmer Lambda 1050 UV/vis/NIR spectrophotometer. Excitation-emission maps were measured with a Horiba J. Y. NanoLog spectrofluorometer using a liquid nitrogen-cooled InGaAs detector array. For FT-IR analysis, the functionalized SWNTs was acidified with 0.5 M HCl to ensure termination with —COOH rather than —COONa. A Jascob FT/IR-4100 Spectrometer with an ATR accessory was employed to record the FT-IR spectra.

Au-Substrated Enhanced Scanning Electron Microscopy:

The water soluble SWNTs were drop-cast on a gold-on-silicon substrate, air dried, and then rinsed with water to remove salts. SEM was performed on a Hitachi SU-70 Schottky field emission gun scanning electron microscope operating at an accelerating voltage of 1 kV with an emission current of 34-35 µA.

Atomic Layer Deposition:

Al$_2$O$_3$ was grown on SWNT-[(CH$_2$)$_5$COOH]$_n$ drop-cast on a lacey carbon copper grid (SPI, West Chester, Pa.) using a BENEQ TFS 500 ALD reactor. Trimethyl aluminum (TMA) and de-ionized water were supplied as alternate 250 ms pulses from room temperature ampoules, separated by 500 ms N$_2$ system purges with the reactor temperature at 150° C. These conditions yielded a growth rate of ~1.0 Å/cycle which was consistent with literature values (George et al., *J. Phys. Chem.* 100:13121-13131 (1996)). TEM was performed on a JEOL JEM 2100 LaB6 transmission electron microscope (Tokyo, Japan) at an accelerating voltage of 200 kV.

Figure 17:
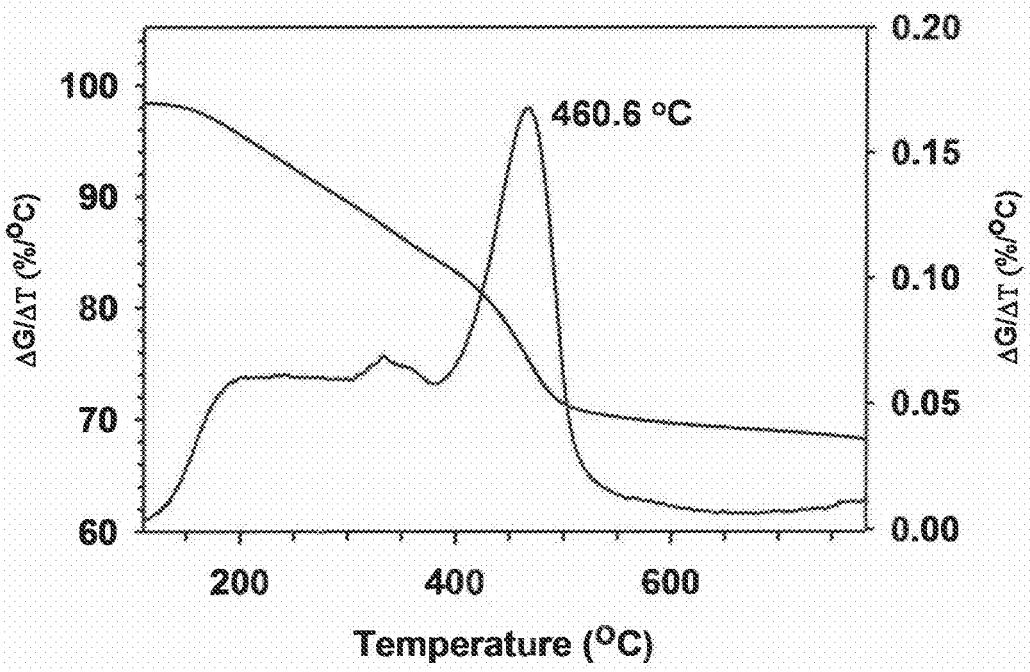
FIG. 17 is a thermogravimetric analysis of HiPco-[(CH$_2$)$_5$COOH]$_n$. Shown is, by example, after 15 cycles of functionalization.

Thermogravimetric analysis: TGA experiments were performed on a TA Instruments Q500 Thermogravimetric Analyzer. The sample was held at 100° C. for 30 min, ramped at 10° C. min$^{-1}$ to 800° C., and then held at 800° C. for 30 min under flowing Ar (100 sccm, 99.9999% purity). The functional group to carbon ratio was calculated according to the weight loss due to the thermally cleaved functional groups (FIG. 17).

Example 3

Figure 18:
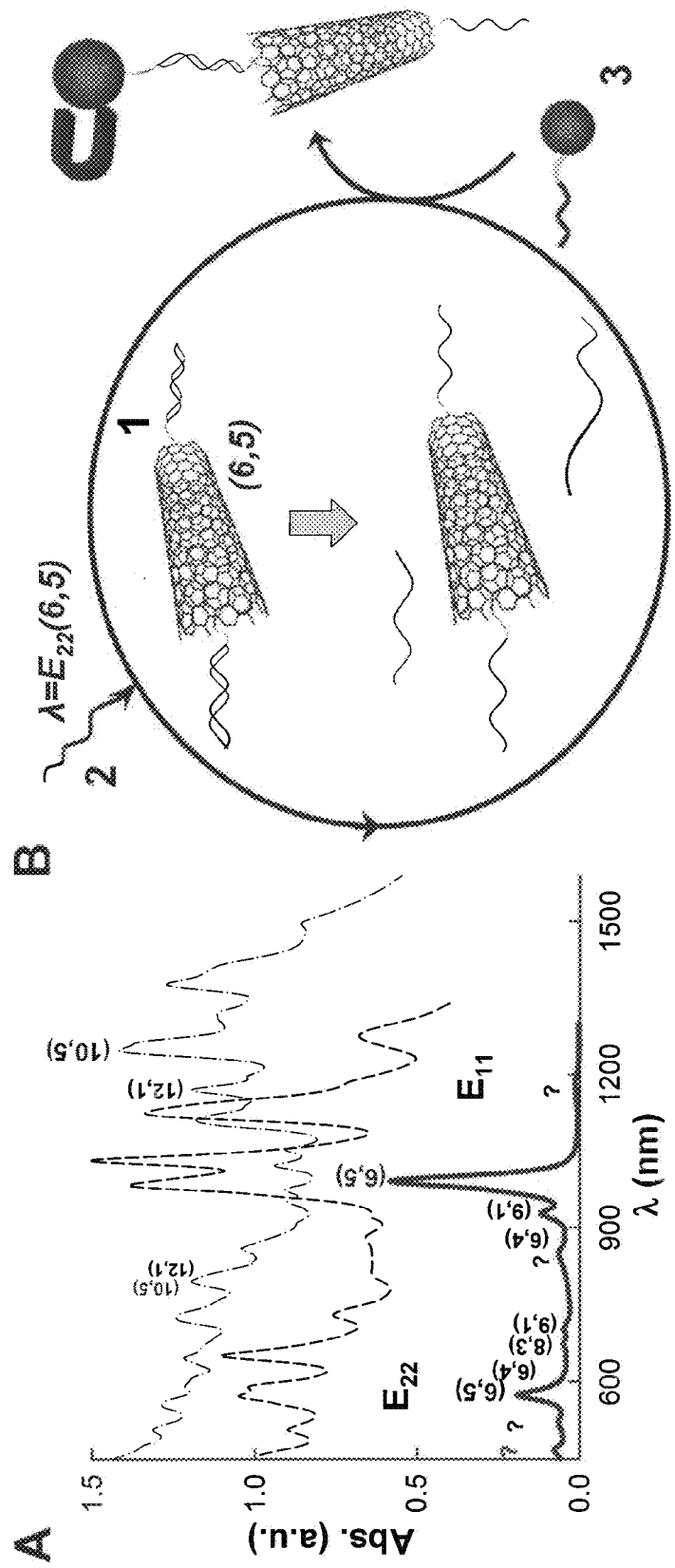
FIG. 18 is optical absorption spectra and schematic illustration showing (n,m)-specific sorting and manipulation of SWNTs by optically selective melting of dsDNA: (A) Optical absorption spectra of SWNTs from different sources: HiPco (dot-dashed line), CoMoCat (dashed line), and purified (6,5)-SWNTs (solid line). The SWNTs were suspended in D$_2$O by surfactants or DNA. The narrow line width (~25 meV at 20° C.) and clean baseline from the purest SWNT sample available (Baughman et al., Science 297:787-792 (2002)) suggest the possibility to optically select a single (n,m) structure from the complex mixture; and (B) Optically-selective heating of a (6,5)-SWNT induces melting of dsDNA that have one of the two constituent ssDNA covalently bonded to the SWNT end. The resulting ssDNA-tagged (6,5)-SWNTs can be separated from the mixture using complementary ssDNA functionalized magnetic beads or other affinity chromatography platform. Changing the laser wavelength allows sorting the SWNTs one specific (n,m) structure at a time.
Figure 20:
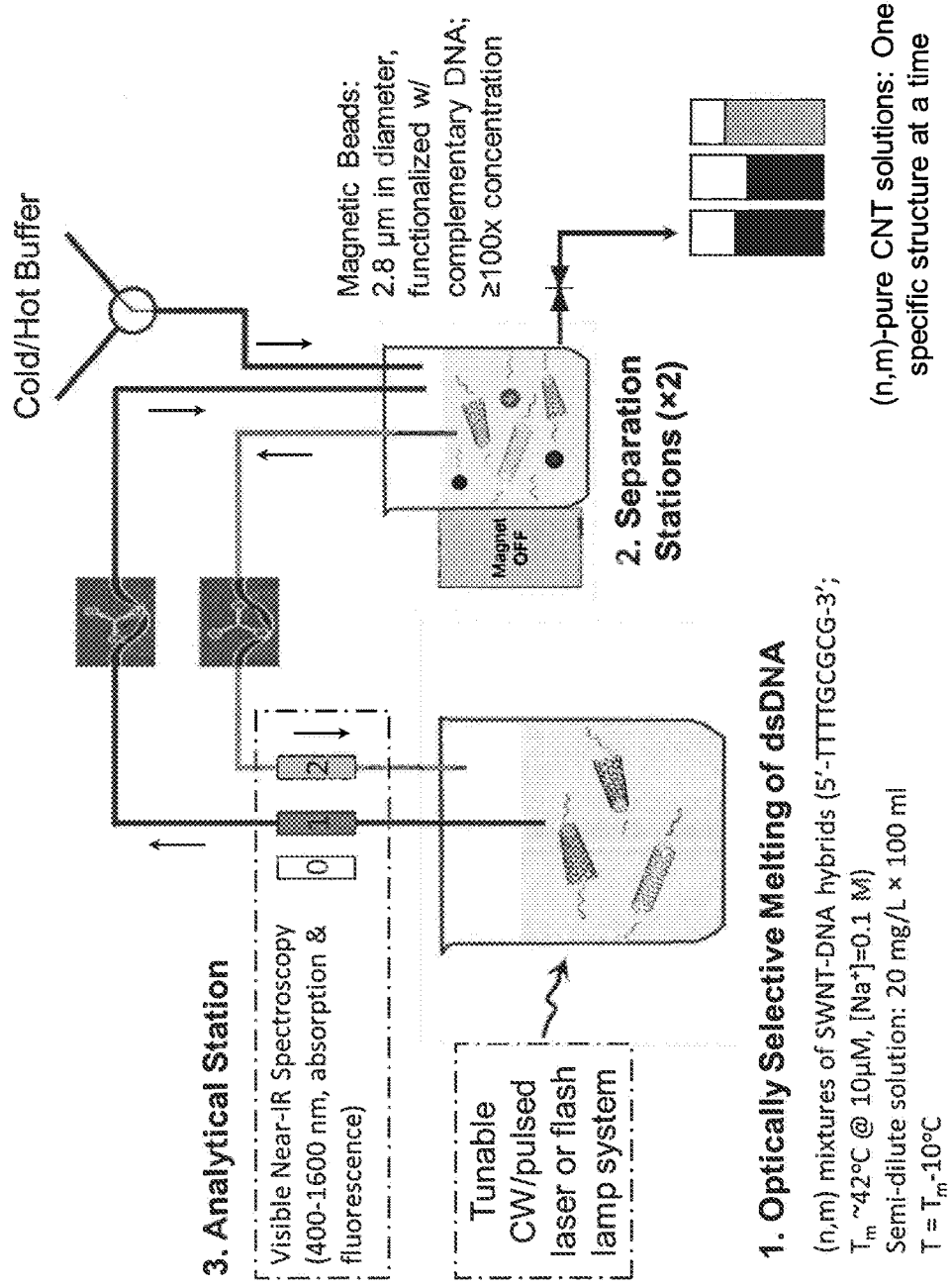
FIG. 20 is a schematic illustration of a method to provide (n,m)-pure CNTs from mixtures of CNTs via optically selective melting of double stranded DNA.

An Optically Selective Approach for Separating and Manipulating Nanotubes by Structure The Biologically-inspired Optically Selective Sorting (BOSS) of this example takes advantage of the electronic and optical properties of SWNTs of a specific chirality to separate them from a mixture of SWNTs (FIG. 18 and FIG. 20).

Unlike the previous separation methods (Hersam, *Nature Nanotechnology* 3:387-394 (2008)), BOSS directly uses the electronic and optical properties of semiconducting SWNTs to effect separation (FIG. 18). First, a double-stranded DNA (dsDNA) is covalently coupled to the ends of SWNTs through one of the two strands following literature methods (Baker et al., *Nano Lett.* 2:1413-1417 (2002)). The SWNT structure of interest is then selectively heated via light absorption at its van Hove transitions—the unique optical "fingerprints" for each (n,m) structure (Bachilo, et al., *Science* 298:2361-2366 (2002)—to melt the dsDNA, while leaving all other nanotubes unaffected. The melting of the dsDNA leaves only the covalently attached ssDNA, which is then used as a recognizable chemical tag for subsequent separation of the selected SWNT via conventional biological methods, e.g., affinity chromatography.

The selectivity of the BOSS route derives from the opto-electronic-induced local heating of SWNTs and the sharp melting transition of the DNA duplexes. The advantage of this strategy is clear when revisiting the example of (10,10) vs. (11,9)-SWNT. Although their diameters and densities are nearly indistinguishable, the former is a metal, while the latter is a semiconductor possessing optical transitions between the so-called van Hove singularities in the electronic density of states. Because each SWNT structure has characteristic electronic transitions (FIG. 18A, solid red line) (Zheng and Semke, *J. Am. Chem. Soc.* 129:6084-6085 (2007); Arnold et al., *Nature Nanotechnology* 1:60-65 (2006)) a SWNT of a particular (n,m) structure can be selectively excited by monochromatic light. Due to the strong electron-phonon coupling, heating of the SWNT occurs efficiently (Oron-Carl et al., *Nano Lett.* 5:1761-1767 (2005); Huxtable et al., *Nature Mater.* 2:731-734 (2003)). The use of DNA allows effective transfer of this optical selectivity to chemical selectivity required for manipulation and separation of SWNTs by their electronic structures. The DNA can be replaced with an inexpensive chemical that possesses thermally sensitive properties or chemical bonds (e.g., a thermoresponsive polymer) (Schild, *Prog. Polym. Sci.* 17:163-249 (1992)).

The key to BOSS is the optically selective local heating of SWNTs of a chosen chirality. To avoid collisions between nanoparticles, the experiment was carried out in a semi-dilute solution. The non-interacting concentration limit is ~250 mg/L for 100 nm long SWNTs (Duggal and Pasquali, *Phys. Rev. Lett.* 96:246104/246101-246104/246104 (2006)). This high concentration limit is practical for large-scale separation.

Figure 19:
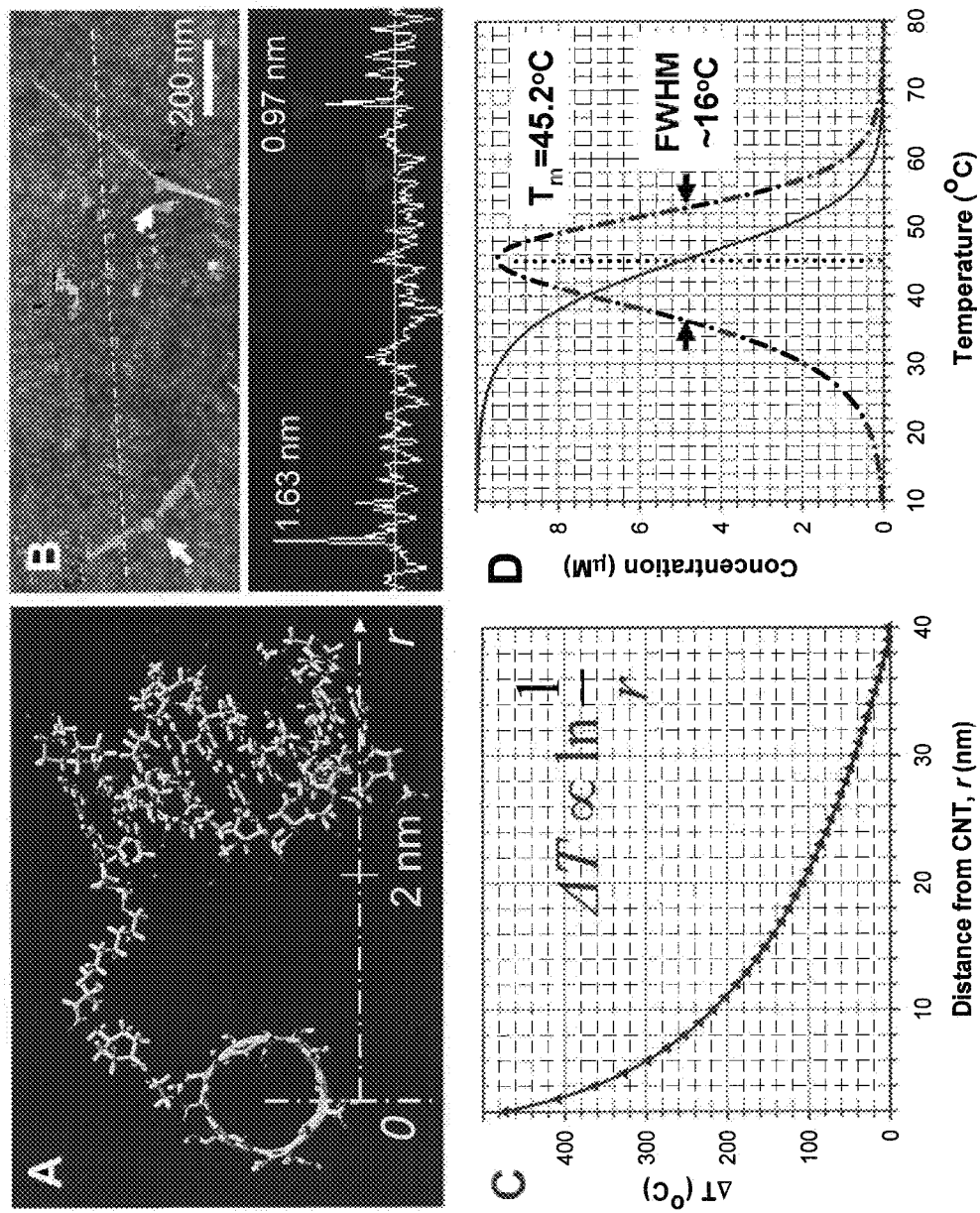
FIG. 19 is two images and two line graphs showing: (A) Molecular structure of a (6,5)-SWNT/dsDNA hybrid, with one of the two constituent ssDNA, e.g., 5'-TTTTGCGCG-3' (SEQ. ID NO: 1), covalently coupled to the SWNT via a heterobifunctional linker; (B) AFM topography image (upper panel) and height profile (lower panel) of SWNT junctions assembled by hybridization of complementary DNA that were covalently coupled to the ends of SWNTs; (C) The temperature at the vicinity of an optically heated (6,5)-SWNT after light irradiation (5 ns, 2.5 mJ laser pulse of λ=568 nm over 1-cm$^2$ area); and (D) The melting profile of the dsDNA. The temperature rise at the vicinity of the SWNT is sufficiently high to induce complete dehybridization of the dsDNA.

Under a modest photon flux, the vicinity of a heated SWNT easily reaches a temperature 50° C. higher than the bulk solution (FIG. 19A, C). By treating the SWNT as a static linear heat source (Carslaw and Jaeger, *Conduction of heat in solids.* 2nd edn, (Oxford University Press, 1959)), the temperature change of the liquid (water or $D_2O$) surrounding the optically heated SWNT, $\Delta T(r)$, is found to drop exponentially as a function of the distance from the SWNT (FIG. 19C). The temperature becomes equalized with that of the bulk solution at 40 nm away. This tight temperature spatial distribution illustrates a strong localization effect of the optically induced heating for the proposed SWNT system. Because the dsDNA has a sharp melting transition (FWHM of first derivative is ~16° C., FIG. 19D), the local heating effect provides a benign mechanism to melt the dsDNA on selected SWNT structures.

To demonstrate the bioactivity for DNA-SWNTs, ssDNA was first covalently coupled to the nanotube ends through a heterobifunctional linker, succinimidyl 4-(N-maleimidomethyl)cyclohexane-1-carboxylate. Two SWNT samples functionalized with complementary DNA were then mixed and allowed to hybridize. FIG. 19B shows SWNT dimers self-assembled through the complementary DNA at the nanotube ends. The efficient formation of SWNT dimers confirms the hybridization capability of the covalently linked ssDNA. This result is consistent with previous work by others (Baker et al., *Nano Lett.* 2:1413-1417 (2002)).

Importantly, the separation of ssDNA-tagged SWNTs can be achieved with commercially available magnetic beads that are functionalized with complementary DNA. The magnetic beads are widely used for biological separation and detection. This approach allows one to take advantage of the highly specific Watson-Crick base pairing and use excess amounts of the reusable magnetic probes to effect separation in a kinetically favorable condition.

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A method comprising:
   a) introducing one or more defects onto one carbon nanotube type or chirality that is part of a mixture of carbon nanotubes by treating said mixture of carbon nanotubes with $H_2O_2$ and HCl; and
   b) reacting said carbon nanotube type or chirality comprising said one or more defects with an alkylating agent selected from the group consisting of dimethyl sulfate, diethyl sulfate, di-n-propyl sulfate, methyl-p-toluenesulfonate, ethyl methanesulfonate, n-propyl methanesulfonate, methyl bromide, ethyl bromide, n-propyl bromide, methyl iodide, ethyl iodide, n-propyl bromide, methyl iodine, and benzyl bromide,
   wherein covalent functionalization of said carbon nanotube type or chirality propagates from said one or more defects to produce a covalently functionalized carbon nanotube type or chirality having alternating sections of functionalized and intact regions of said covalently functionalized carbon nanotube.

2. The method of claim 1, wherein said reacting comprises combining said carbon nanotube comprising said one or more defects, said alkylating agent, liquid ammonia, and an alkali metal.

3. The method of claim 1, wherein said one or more defects are introduced onto a metallic single-walled carbon nanotube.

4. The method of claim 1, wherein said one or more defects are introduced onto a small-diameter single-walled carbon nanotube.

5. The method of claim 1, wherein said alkylating agent is selected from the group consisting of dimethyl sulfate, diethyl sulfate, di-n-propyl sulfate, methyl-p-toluenesulfonate, ethyl methanesulfonate, and n-propyl methanesulfonate.

6. The method of claim 1, wherein said alkylating agent is selected from the group consisting of methyl bromide, ethyl bromide, n-propyl bromide, methyl iodide, ethyl iodide, n-propyl bromide, methyl iodine, and benzyl bromide.

* * * * *

SEQUENCE LISTING

```
<160> NUMBER OF SEQ ID NOS: 1

<210> SEQ ID NO 1
<211> LENGTH: 9
<212> TYPE: DNA
<213> ORGANISM: Artificial sequence
<220> FEATURE:
<223> OTHER INFORMATION: ssDNA tag

<400> SEQUENCE: 1 ttttgcgcg                                                        9
```